(12) United States Patent
Baldino et al.

(10) Patent No.: US 8,546,557 B2
(45) Date of Patent: Oct. 1, 2013

(54) METHODS OF MAKING NUCLEOSIDE TETRAPHOSPHATE ANALOGS

(75) Inventors: Carmen M. Baldino, Woburn, MA (US); Dan P. Cook, Cardiff-By-The-Sea, CA (US); Shomir Ghosh, Brookline, MA (US); Lazlo Varady, Newton, MA (US); Thomas Andreas Waldbach, Neuengonna (DE); Zhongguo Wang, Lexington, MA (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 327 days.

(21) Appl. No.: 12/867,879

(22) PCT Filed: Feb. 13, 2009

(86) PCT No.: PCT/US2009/034018
§ 371 (c)(1),
(2), (4) Date: Nov. 5, 2010

(87) PCT Pub. No.: WO2009/102928
PCT Pub. Date: Aug. 20, 2009

(65) Prior Publication Data
US 2011/0046362 A1    Feb. 24, 2011

Related U.S. Application Data

(60) Provisional application No. 61/029,074, filed on Feb. 15, 2008.

(51) Int. Cl.
*C07H 19/00* (2006.01)
*C07H 19/20* (2006.01)

(52) U.S. Cl.
USPC .................................... 536/26.21; 536/26.22

(58) Field of Classification Search
None
See application file for complete search history.

(56) References Cited

U.S. PATENT DOCUMENTS

| 7,223,744 B2 * | 5/2007 | Yerxa et al. | 514/47 |
| 2005/0085439 A1 | 4/2005 | Yerza et al. | 514/50 |

FOREIGN PATENT DOCUMENTS

| WO | WO 03/001185 | 2/2003 |
| WO | WO 2008/060632 | 5/2008 |

OTHER PUBLICATIONS

International Search Report and Written Opinion, dated May 24, 2011, PCT/US2009/34018 (18 PGS).
Shimazu et al., "Facile Synthesis of Nucleotides Containing Polyphosphates by Mn(II) and Cd(II) Ion-Catalyzed Pyrophosphate Bond Formation in Aqueous Solution", Tetrahedron Letters, vol. 31, No. 2, pp. 235-238, 1990.
Reiss et al., "Dismutation Reactions of Nucleoside Polyphosphates. III. The Synthesis of α,ω-Dinucleoside 5'-Polyphosphates", α,ω-Dinucleoside 5'-Polyphosphates, Contribution No. 24 from the Syntex Institute of Molecular Biology, Stanford Industrial Park, Palo Alto, CA, Oct. 1965, pp. 3381-3387.
Sood et al., "Terminal Phosphate-Labeled Nucleotides with Improved Substrate Properties for Homogeneous Nucleic Acid Assays", GE Healthcare, J. Am. Chem. Soc. 2005, 127, pp. 2394-2395, Oct. 21, 2004.
Ng et al., "The action of a water-soluble carbodiimide on adenosine-5'-polyphosphates", Nucleic Acids Research, vol. 15, No. 8, 1987, pp. 3573-3580.
Han et al., "One-Flask Synthesis of Dinucleoside Tetra- and Pentaphosphates", Organic Letters 2006, vol. 8, No. 10, pp. 2075-2077.
Nottbohm et al., "A Colorimetric Substrate for Poly(ADP-Ribose) Polymerase-1, VPARP, and Tankyrase-1", Enzyme Kinetics, Angew. Chem. Int. Ed. 2007, 46, pp. 2066-2069.
Woenckhaus et al., "Synthesis and biochemical properties of nicotinamide-phenyl-dinucleo tide", Chemische Berichte, May 1966, vol. 99, No. 5, May 1966, pp. 1712-1717.
Mazzella et al., "Mechanistic Diagnoses of N-Ribohydrolases and Purine Nucleoside Phosphorylase", J. Am. Chem. Soc. 1996, 118, pp. 2111-2112.
Patent Examination Report No. 1 issued in corresponding application No. 2009214591, dated Apr. 29, 2013 (3 pgs).

\* cited by examiner

*Primary Examiner* — Lawrence E Crane
(74) *Attorney, Agent, or Firm* — Hayes Soloway P.C.

(57) ABSTRACT

The invention provides compounds and methods for making adenosine-ribofuranoside tetraphosphate compounds. The compounds are contemplated to have activity at the P2Y receptor and may be used in the treatment of medical disorders such as cystic fibrosis and upper respiratory disorders.

72 Claims, No Drawings

US 8,546,557 B2

METHODS OF MAKING NUCLEOSIDE TETRAPHOSPHATE ANALOGS

RELATED APPLICATIONS

This application claims the benefit of priority to U.S. Provisional Patent Application Ser. No. 61/029,074, filed Feb. 15, 2008, the contents of which are hereby incorporated by reference.

FIELD OF THE INVENTION

The present invention provides compounds and methods for making adenosine tetraphosphate compounds. In particular, the present invention provides compositions and methods for making adenosine-ribofuranoside tetraphosphate compounds.

BACKGROUND OF THE INVENTION

P2Y2 receptors are present on the body's mucosal surfaces, including the lungs, eyes, upper airways, mouth, vaginal tract and gastrointestinal tract, and on non-mucosal surfaces, such as the retinal pigment epithelium (RPE). The P2Y2 receptor coordinates the entire mechanism of mucociliary clearance in the upper portion of the lower respiratory and digestive tract. This process can be regulated therapeutically by local delivery of molecules that bind to and activate these receptors.

P2Y2 receptors are found on each of the three principal cell types that line the airways: ciliated epithelial cells, goblet cells, and Type II alveolar cells. Upon activation of the P2Y2 receptor on ciliated epithelial cells, salt and water are released from the cell, mucous secretions are hydrated, and ciliary beat frequency is increased. Activation of the P2Y2 receptor on goblet cells modulates the release of mucin. And when the P2Y2 receptors on Type II alveolar cells are activated, surfactant is released, maintaining the surface tension of the smallest peripheral airways and preventing their collapse.

Activation of mucosal hydration and mucociliary clearance in the lungs and upper airways via P2Y2 modulators provides opportunities for treating diseases like cystic fibrosis and upper respiratory disorders involving nasal symptoms like congestion, pressure and nasal blockage. These upper respiratory disorders include rhinosinusitis, allergic rhinitis, and upper respiratory infections like the common cold and influenza. Also, increasing mucociliary clearance in the lungs allows for non-invasive collection of mucus samples from the lungs, which may be beneficial in the diagnosis of lung cancer.

Chronic obstructive pulmonary disease (COPD) is characterized by mucus secretion retention in the lungs, resulting in progressive lung dysfunction over time. Many patients diagnosed with COPD have a disorder called chronic bronchitis (CB). Cystic fibrosis and Primary Ciliary Dyskinesia (PCD) are other examples of lung disorders that have a clinical profile similar to COPD. Primary or secondary ciliary dyskinesia results in retained secretions that can only be cleared by coughing. Most patients with COPD utilize coughing to help clear retained secretions because of impaired mucociliary clearance.

Sinusitis, also characterized by an accumulation of retained mucous secretions, is an inflammation of the paranasal sinuses typically associated with an upper respiratory infection. This condition affects many people in the US.

Otitis media (OM) is a viral or bacterial infection of the middle ear, primarily afflicting children under the age of three. It is usually precipitated by an upper respiratory infection that spreads into the middle ear via the nasopharynx and eustachian tube. Following antibiotic treatment, accumulated fluid in the middle ear causes hearing impairment and potential language and cognitive development delays. Improved clearing of middle ear secretions would reduce or eliminate significant sequelae of otitis media.

Pneumonia is an illness of the respiratory system that is linked to retained secretions. This illness afflicts many people each year and is a leading cause of death for chronically ill patients. Amongst those at risk for developing pneumonia, patients that are immobilized generally have a high risk of developing the illness.

At times, it is therapeutically desirable to increase drainage of the lacrimal system because improper functioning of the lacrimal drainage system can result in excessive tearing (epiphora), mucopurulent discharge, and/or recurrent dacryocystitis. Current treatments for nasolacrimal duct obstruction are mostly invasive surgical procedures, which are not desirable. Tear secretion can be stimulated from lacrimal accessory tissues via P2Y2 and/or P2Y4 purinergic receptor-mediated mechanisms similar to those which hydrate airway epithelia. Dry eye disease is the general term for indications produced by abnormalities of the precorneal tear film characterized by a decrease in tear production or an increase in tear film evaporation, together with the ocular surface disease that results. The current pharmaceutical treatment of dry eye disease is often limited to administration of artificial tears (saline solution) to temporarily rehydrate the eyes. This treatment generally provides only short-term relief, and frequent dosing is necessary.

Normally, mucous secretions are removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus. Secretory functions of the uterine, cervical and vaginal mucous cells also have a profound impact on the function and health of the reproductive tract. For example, the quality and quantity of cervical mucus changes throughout the menstrual cycle and such changes dramatically influence fertility. Under the influence of rising estrogen levels, cervical mucus becomes thin, allowing the passage of spermatozoa. Later in the menstrual cycle, as progesterone levels increase, mucus becomes thick and hostile to sperm penetration, thereby closing the window of fertility. Such thickening of cervical mucus is thought to be one of the primary modes of contraceptive action for progestin-only contraceptives.

Accordingly, the need exists for developing new and improved methods of making compounds that act at P2Y receptors, e.g., $P2Y_1$ or $P2Y_2$ receptor.

SUMMARY

One aspect of the invention provides a method of making an organophosphate compound, comprising admixing a compound of formula I-A and a compound of formula I-A to form a compound of formula III-A, wherein formula I-A is represented by:

I-A

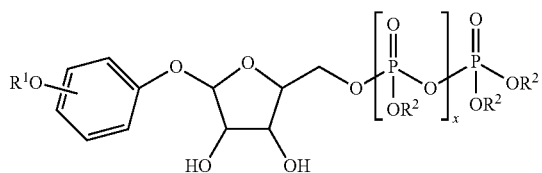

wherein:
$R^1$ is $C_1$-$C_4$ alkyl;
$R^2$ represents independently for each occurrence H or an alkali metal; or two occurrences of $R^2$ taken together form an alkaline earth metal; and
x is 0, 1, or 2;
formula II-A is represented by:

II-A

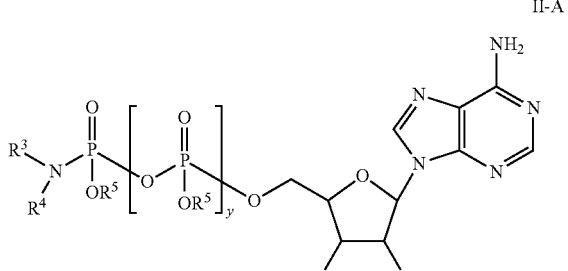

wherein:
$R^3$ and $R^4$, taken together with the nitrogen atom to which they are attached, form a 3 to 6 membered heterocyclic ring;
$R^5$ represents independently for each occurrence H or an alkali metal; or two occurrences of $R^5$ taken together form an alkaline earth metal;
y is 0, 1, or 2; and
provided that the sum of x and y is 2; and
formula III is represented by:

$R^7$ represents independently for each occurrence H or an alkali metal; or two occurrences of $R^7$ taken together form an alkaline earth metal.
In certain aspects, $R^7$ is H, Na, or K.
In certain aspects, compound of formula I-A is represented by:

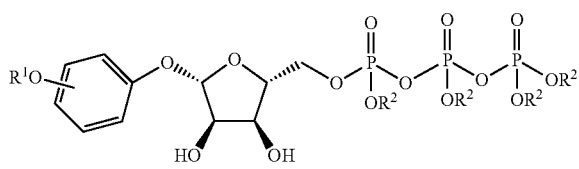

wherein:
$R^1$ is $C_1$-$C_4$ alkyl; and
$R^2$ represents independently for each occurrence H or an alkali metal.
In certain aspects, compound of formula II-A is represented by:

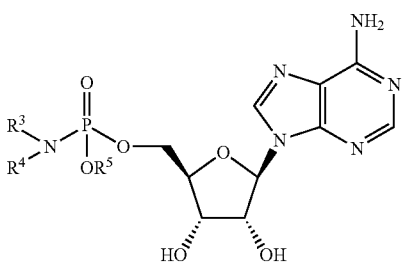

wherein:
$R^3$ and $R^4$, taken together with the nitrogen atom to which they are attached, form a 3 to 6 membered heterocyclic ring; and
$R^5$ represents independently for each occurrence H or an alkali metal.

III

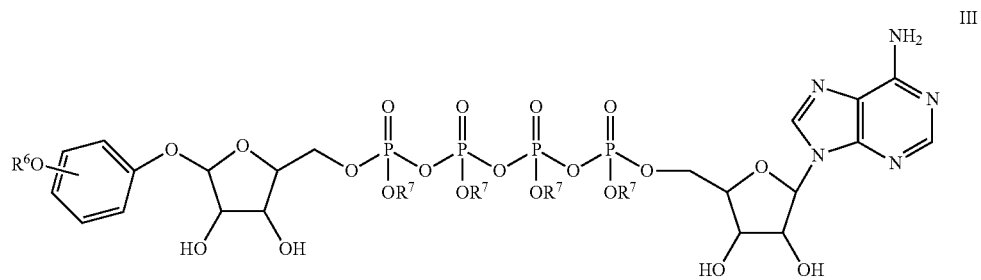

wherein:
$R^6$ is $C_1$-$C_4$ alkyl; and

In certain aspects, compound of formula III is represented by:

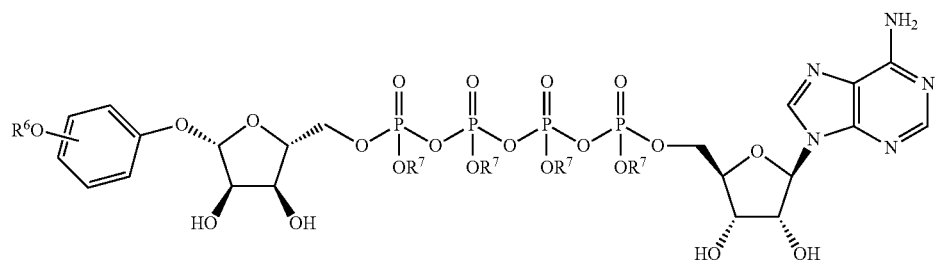

wherein
$R^6$ is $C_1$-$C_4$ alkyl; and
$R^7$ represent independently for each$_{occurrence}$ H or an alkali metal.

In certain aspects, Compound of formula I-A is represented by:

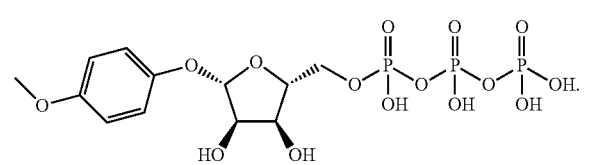 [SMILES: COc1ccc(O[C@@H]2O[C@H](COP(=O)(O)OP(=O)(O)OP(=O)(O)O)[C@@H](O)[C@H]2O)cc1]

In certain aspects, compound of formula II-A is represented by:

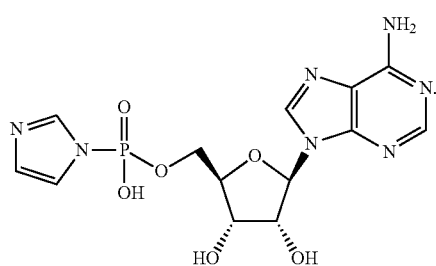 [SMILES: Nc1ncnc2c1ncn2[C@@H]1O[C@H](COP(=O)(O)n2ccnc2)[C@@H](O)[C@H]1O]

In certain aspects, compound of formula III is represented by:

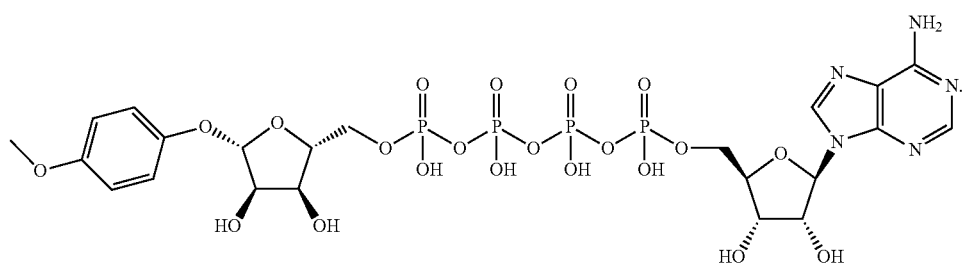 [SMILES: COc1ccc(O[C@@H]2O[C@H](COP(=O)(O)OP(=O)(O)OP(=O)(O)OP(=O)(O)OC[C@H]3O[C@@H](n4cnc5c(N)ncnc54)[C@H](O)[C@@H]3O)[C@@H](O)[C@H]2O)cc1]

In certain aspects, the method further comprises admixing a Lewis acid.

In certain aspects, the Lewis acid is $MnX_2$, wherein X is halogen.

In certain aspects, the Lewis acid is $MnCl_2$, $NiCl_2$, $ZnCl_2$, or $MgCl_2$.

In certain aspects, the method further comprises admixing a compound of formula III-A and an alkylating agent to form a compound of formula IV-A, wherein formula IV-A is represented by:

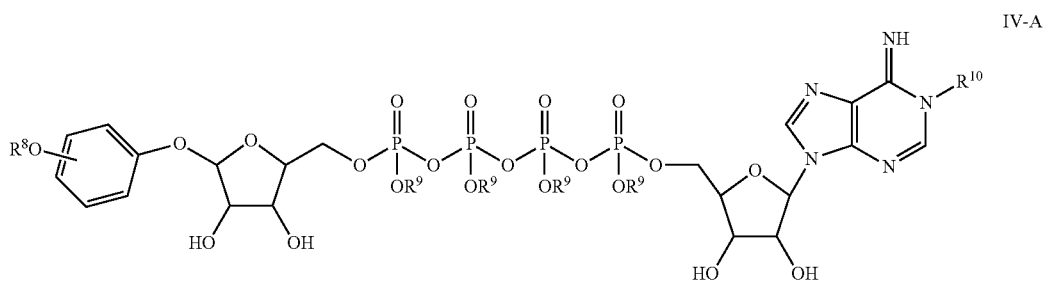

IV-A wherein:

$R^8$ and $R^{10}$ represent independently $C_1$-$C_4$ alkyl; and $R^9$ represents independently for each occurrence H or an alkali metal; or two occurrences of $R^9$ taken together form an alkaline earth metal.

In certain aspects, compound of formula IV-A is represented by:

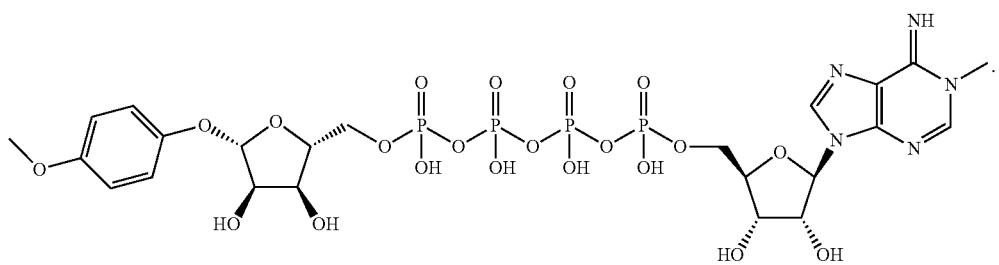

In certain aspects, the alkylating agent is R—X, wherein R is methyl and X is bromide, iodide, mesylate, tosylate, or triflate.

In certain aspects, compound of formula I-A is represented by:

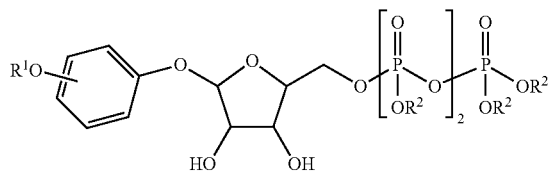

I-A wherein:

$R^1$ is $C_1$-$C_4$ alkyl; and $R^2$ represents independently for each occurrence H or an alkali metal; or two occurrences of $R^2$ taken together form an alkaline earth metal.

In certain aspects, the method further comprises admixing a compound of formula V-A and R'O—P(O)(OR')—O—P(O)(OR')$_2$ and a phosphate coupling agent to form the compound of formula I-A, wherein R' is H or an alkali metal, and formula V-A is represented by:

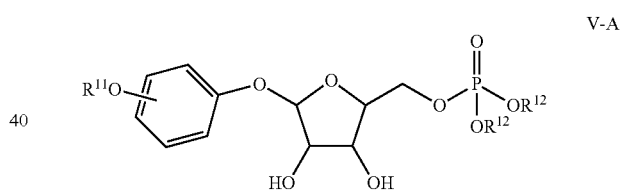

V-A wherein:

$R^{11}$ is $C_1$-$C_4$ alkyl; and $R^{12}$ represents independently for each occurrence H or an alkali metal; or two occurrences of $R^{12}$ taken together form an alkaline earth metal.

In certain aspects, compound of formula V-A is represented by:

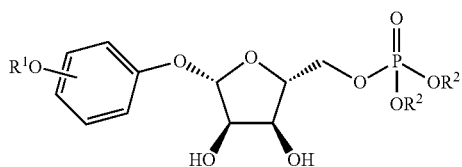

wherein:

$R^{11}$ is $C_1$-$C_4$ alkyl; and $R^{12}$ represents independently for each occurrence H or an alkali metal; or two occurrences of $R^{12}$ taken together form an alkaline earth metal.

In certain aspects, compound of formula V-A is represented by

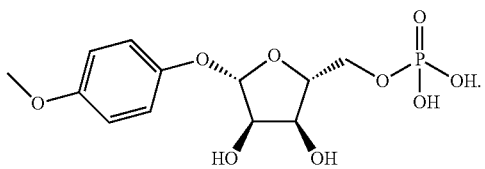 [SMILES: COc1ccc(O[C@@H]2O[C@H](COP(=O)(O)O)[C@@H](O)[C@H]2O)cc1]

In certain aspects, the phosphate coupling agent is 1,1'-carbonyldiimidazole.

In certain aspects, the method further comprises admixing a compound of formula VI-A and a phosphorylating agent to form the compound of formula V-A, wherein formula VI-A is represented by:

VI-A

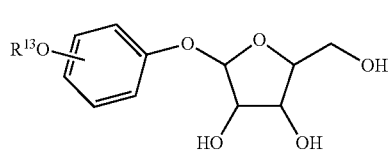

wherein, $R^{13}$ is $C_1$-$C_4$ alkyl.

In certain aspects, said compound of formula VI-A is represented by:

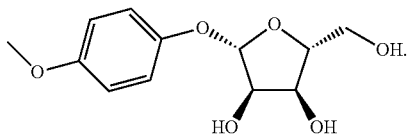 [SMILES: COc1ccc(O[C@@H]2O[C@H](CO)[C@@H](O)[C@H]2O)cc1]

In certain aspects, the phosphorylating agent is $P(O)(O\text{-alkyl})_3$.

In certain aspects, the method further comprises admixing $P(O)X_3$, wherein X is a halogen.

In certain aspects, the method further comprises admixing $P(O)Cl_3$.

In certain aspects, the method further comprises admixing a compound of formula VII-A and an acyl-deprotecting agent to form a compound of formula VI-A, wherein formula VII-A is represented by:

VII-A

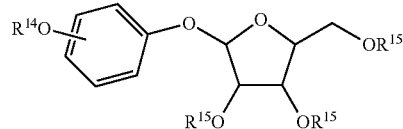

wherein:
$R^{14}$ is $C_1$-$C_4$ alkyl;
$R^{15}$ represents independently for each occurrence —C(O)alkyl, —C(O)aryl, or —C(O)aralkyl.

In certain aspects, compound of formula VII-A is represented by:

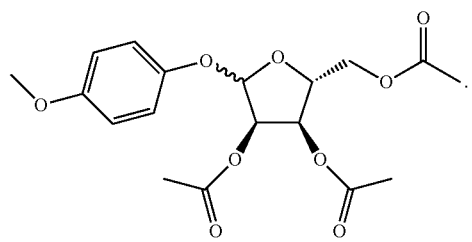 [SMILES: COc1ccc(OC2O[C@H](COC(C)=O)[C@@H](OC(C)=O)[C@H]2OC(C)=O)cc1]

In certain aspects, the acyl-deprotecting agent is a mixture of a base and a C1-C6 alcohol.

In certain aspects, the deprotecting agent is a mixture of $NH_3$ and MeOH.

In certain aspects, the method further comprises admixing a compound of formula VIII-A, an alkoxyphenol, and a Lewis acid to form the compound of formula VII-A, wherein formula VIII-A is represented by:

VIII-A

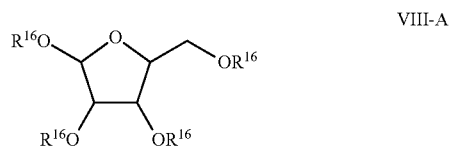

wherein $R^{16}$ represents independently for each occurrence —C(O)alkyl, —C(O)aryl, or —C(O)aralkyl.

In certain aspects, compound of formula VIII-A is represented by:

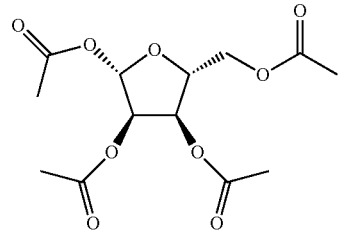 [SMILES: CC(=O)OC[C@H]1O[C@@H](OC(C)=O)[C@H](OC(C)=O)[C@@H]1OC(C)=O]

In certain aspects, the Lewis acid is $SnCl_4$ or $TiCl_4$.

In certain aspects, compound of formula I-A is represented by:

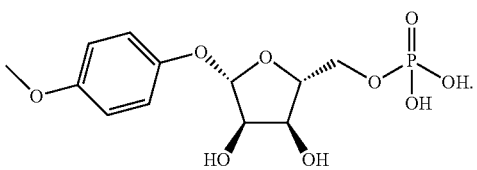 [SMILES: COc1ccc(O[C@@H]2O[C@H](COP(=O)(O)O)[C@@H](O)[C@H]2O)cc1]

In certain aspects, compound of formula II-A is represented by:

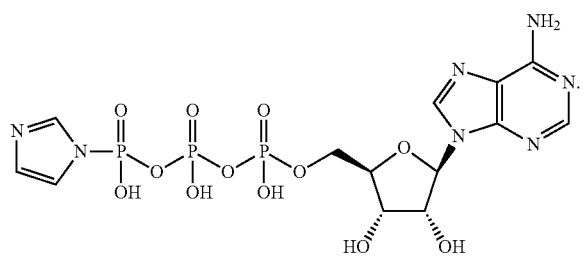 [SMILES: Nc1ncnc2c1ncn2[C@@H]1O[C@H](COP(=O)(O)OP(=O)(O)OP(=O)(O)n2ccnc2)[C@@H](O)[C@H]1O]

In certain aspects, compound of formula I-A is represented by:

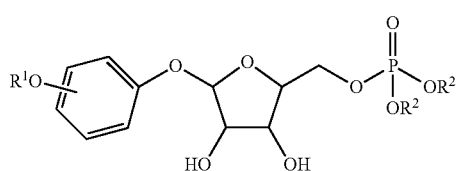

wherein:
$R^1$ is $C_1$-$C_4$ alkyl; and
$R^2$ represents independently for each occurrence H or an alkali metal; or two occurrences of $R^2$ taken together form an alkaline earth metal.

In certain aspects, the method comprises admixing a compound of formula VI-A and a phosphorylating agent to form the compound of formula I-A, wherein formula VI-A is represented by:

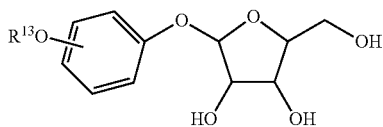

wherein, $R^{13}$ is $C_1$-$C_4$ alkyl.

In certain aspects, compound of formula VI-A is represented by:

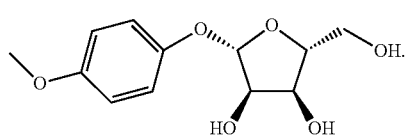 [SMILES: COc1ccc(O[C@@H]2O[C@H](CO)[C@@H](O)[C@H]2O)cc1]

In certain aspects, the phosphorylating agent is P(O)(O-alkyl)$_3$.

In certain aspects, the method further comprises admixing P(O)X$_3$, wherein X is a halogen.

In certain aspects, the method further comprises admixing P(O)Cl$_3$.

In certain aspects, the method further comprises admixing a compound of formula VII-A and an acyl-deprotecting agent to form a compound of formula VI-A, wherein formula VII-A is represented by:

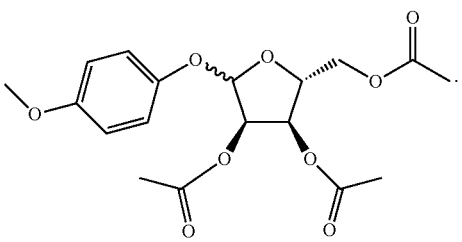

wherein:
$R^{14}$ is $C_1$-$C_4$ alkyl; and
$R^{15}$ represents independently for each occurrence —C(O)alkyl, —C(O)aryl, or —C(O)aralkyl.

In certain aspects, compound of formula VII-A is represented by:

[structure]

In certain aspects, the acyl-deprotecting agent is a mixture of a base and a $C_1$-$C_6$ alcohol.

In certain aspects, the acyl-deprotecting agent is a mixture of NH$_3$ and MeOH.

In certain aspects, the method comprises admixing a compound of formula VIII-A, an alkoxyphenol, and a Lewis acid to form the compound of formula VII-A, wherein formula VIII-A is represented by:

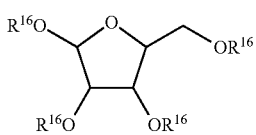

wherein $R^{16}$ represents independently for each occurrence —C(O)alkyl, —C(O)aryl, or —C(O)aralkyl.

In certain aspects, compound of formula VIII-A is represented by:

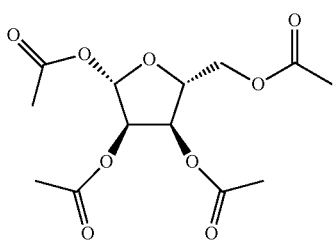 [SMILES: CC(=O)OC[C@H]1O[C@@H](OC(C)=O)[C@H](OC(C)=O)[C@@H]1OC(C)=O]

In certain aspects, the Lewis acid is SnCl$_4$, TiCl$_4$, ZnCl$_2$, AlCl$_3$, CuCl$_2$, FeCl$_3$, or BF$_3$.Et$_2$O.

In certain aspects, the Lewis acid is SnCl$_4$ or TiCl$_4$.

Another aspect of the invention provides a method of making an organophosphate compound, comprising admixing a compound of formula I-C and a compound of formula II-C to form a compound of formula III, wherein formula I-C is represented by:

formula II-C is represented by:

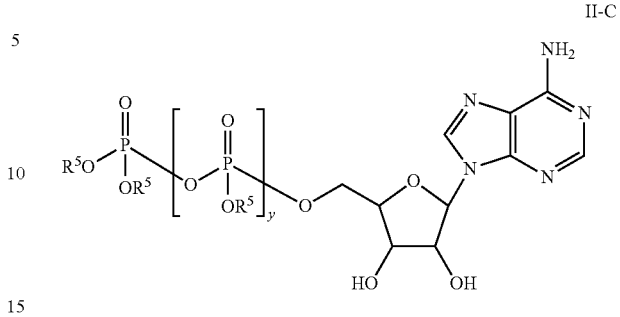

wherein:
R$^5$ represents independently for each occurrence H or an alkali metal; or two occurrences of R$^5$ taken together form an alkaline earth metal;
y is 1 or 2; and
provided that the sum of x and y is 2; and
formula III is represented by:

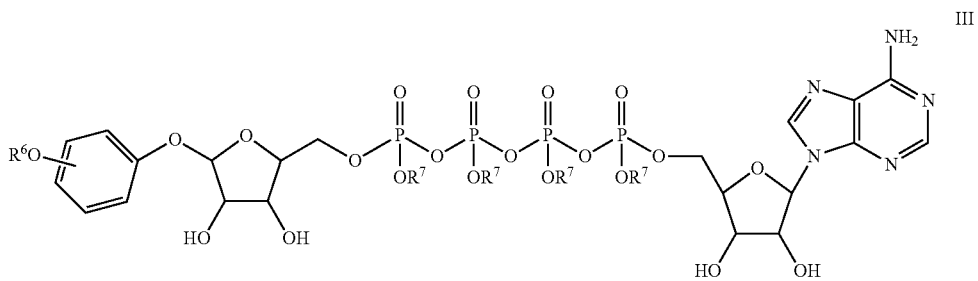

wherein:
R$_1$ is C$_1$-C$_4$ alkyl; and
R$^2$ represents independently for each occurrence H or an alkali metal; or two occurrences of R$^2$ taken together form an alkaline earth metal.

In certain aspects, R$^7$ is H, Na, or K.

In certain aspects, compound of formula I-C is represented by:

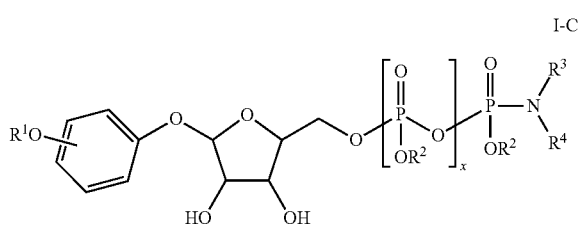

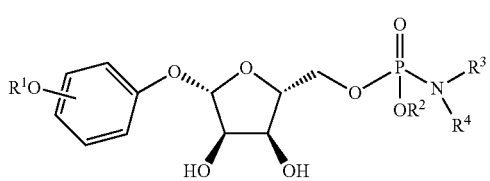

wherein:
R$^1$ is C$_1$-C$_4$ alkyl;
R$^2$ represents independently for each occurrence H or an alkali metal; or two occurrences of R$^2$ taken together form an alkaline earth metal;
R$^3$ and R$^4$, taken together with the nitrogen atom to which they are attached, form a 3 to 6 membered heterocyclic ring; and
x is 0 or 1;

wherein:
R$^1$ is C$_1$-C$_4$ alkyl;
R$^2$ represents independently for each occurrence H or an alkali metal; and
R$^3$ and R$^4$, taken together with the nitrogen atom to which they are attached, form a 3 to 6 membered heterocyclic ring.

In certain aspects, compound of formula II-C is represented by:

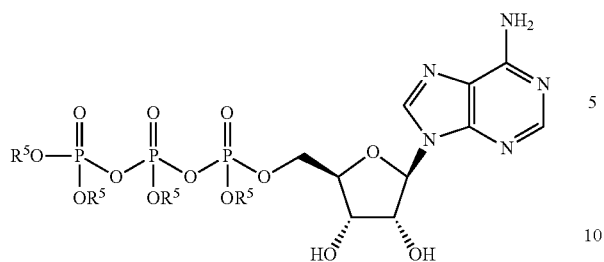

wherein, $R^5$ represents independently for each occurrence H or an alkali metal.

In certain aspects, compound of formula III is represented by:

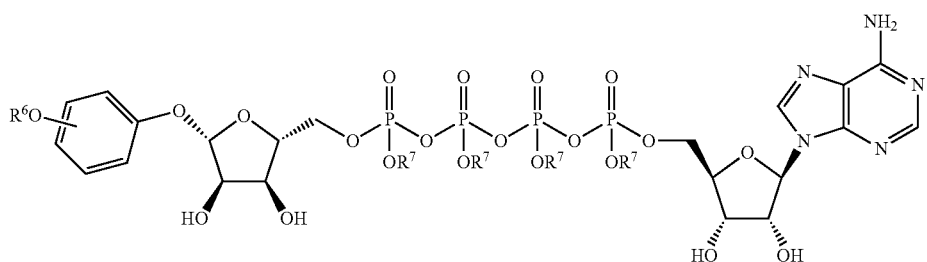

wherein:

$R^6$ is $C_1$-$C_4$ alkyl; and $R^7$ represents independently for each occurrence H or an alkali metal.

In certain aspects, compound of formula I-C is represented by:

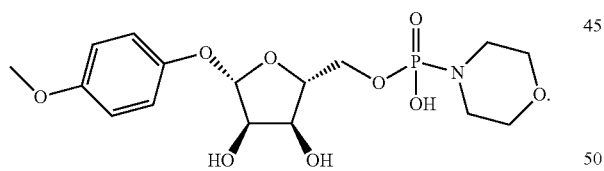

In certain aspects, compound of formula II-C is represented by:

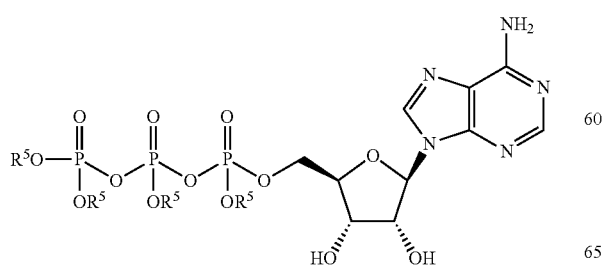

wherein, $R^2$ represents independently for each occurrence H or Na.

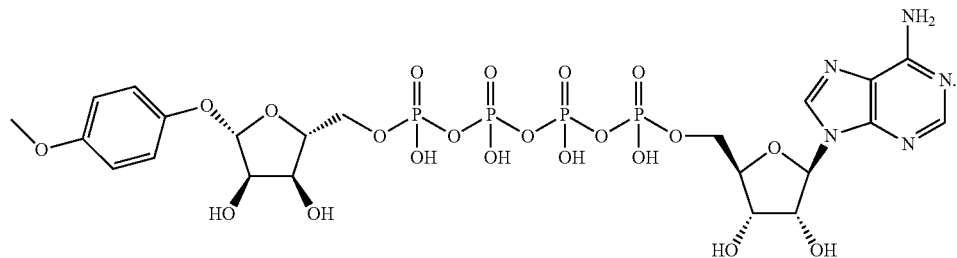 [SMILES: COc1ccc(O[C@@H]2O[C@H](COP(=O)(O)OP(=O)(O)OP(=O)(O)OP(=O)(O)OC[C@H]3O[C@@H](n4cnc5c(N)ncnc54)[C@H](O)[C@@H]3O)[C@@H](O)[C@H]2O)cc1]

In certain aspects, the method further comprises admixing a Lewis acid.

In certain aspects, the Lewis acid is $MnCl_2$.

In certain aspects, the method further comprises admixing a compound of formula III and an alkylating agent to form a compound of formula IV-C, wherein formula IV-C is represented by:

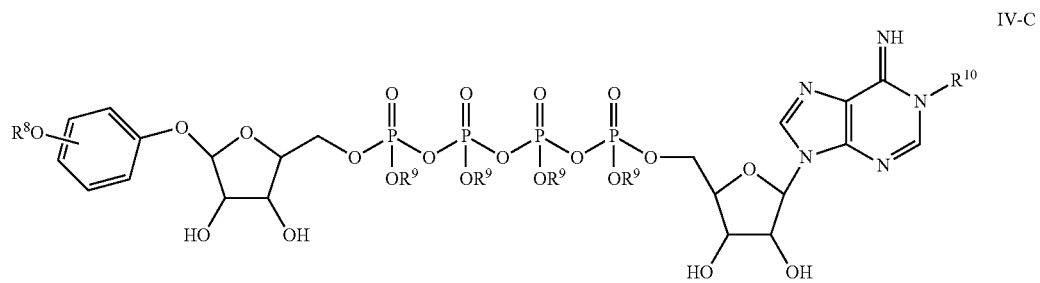

IV-C wherein:
$R^8$ and $R^{10}$ represent independently $C_1$-$C_4$ alkyl; and
$R^9$ represents independently for each occurrence H or an alkali metal; or two occurrences of $R^9$ taken together form an alkaline earth metal.

In certain aspects, compound of formula IV-C is represented by:

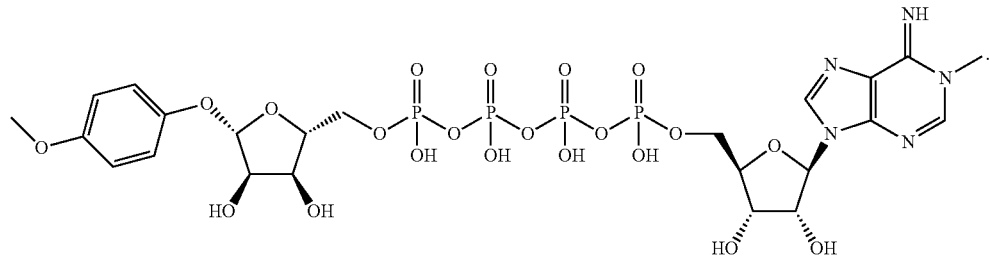

In certain aspects, the alkylating agent is R—X, wherein R is methyl and X is bromide, iodide, mesylate, tosylate, or triflate.

In certain aspects, the method further comprises admixing a compound of formula V-C, morpholine, and a carbodiimide coupling agent to form the compound of formula I-C, wherein formula V-C is represented by:

In certain aspects, compound of formula III is represented by:

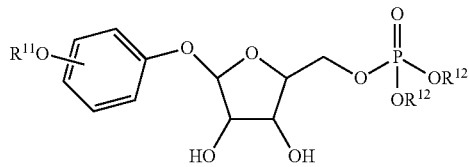

V-C further comprising $N(R^{13})_4$ salts thereof;
wherein:
$R^{11}$ is $C_1$-$C_4$ alkyl;
$R^{12}$ represents independently for each occurrence H or an alkali metal; or two occurrences of $R^{12}$ taken together form an alkaline earth metal; and
$R^{13}$ represents independently for each occurrence H or $C_1$-$C_4$ alkyl.

In certain aspects, compound of formula V-C is represented by:

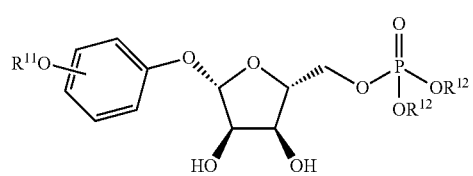

further comprising $N(R^{13})_4$ salts thereof;
wherein:
$R^{11}$ is $C_1$-$C_4$ alkyl;
$R^{12}$ represents independently for each occurrence H or an alkali metal; or two occurrences of $R^{12}$ taken together form an alkaline earth metal; and
$R^{13}$ represents independently for each occurrence H or $C_1$-$C_4$ alkyl.

In certain aspects, compound of formula V-C is represented by:

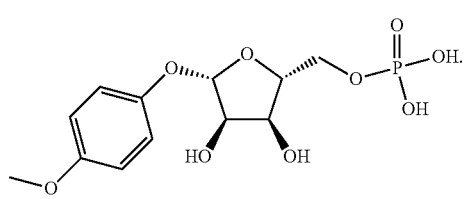 [SMILES: COc1ccc(O[C@@H]2O[C@H](COP(=O)(O)O)[C@@H](O)[C@H]2O)cc1]

In certain aspects, the carbodiimide coupling agent is N,N'-dicyclohexylcarbodiimide.

In certain aspects, the method comprises admixing a compound of formula VI-C and a phosphorylating agent to form the compound of formula V-C, wherein formula VI-C is represented by:

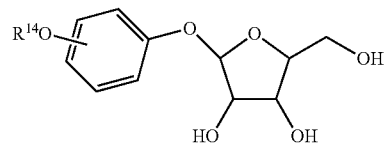

VI-C wherein, $R^{14}$ is $C_1$-$C_4$ alkyl.

In certain aspects, compound of formula VI-C is represented by

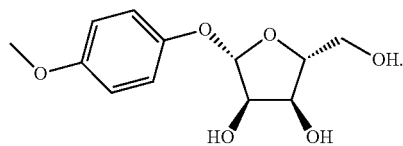 [SMILES: COc1ccc(O[C@@H]2O[C@H](CO)[C@@H](O)[C@H]2O)cc1]

In certain aspects, the phosphorylating agent is $P(O)(O\text{-alkyl})_3$.

In certain aspects, the method further comprises admixing $P(O)X_3$, wherein X is halogen.

In certain aspects, the method further comprises admixing $P(O)Cl_3$.

In certain aspects, the method further comprises admixing a compound of formula VII-C and an acyl-deprotecting agent to form a compound of formula VI-C, wherein formula VII-C is represented by:

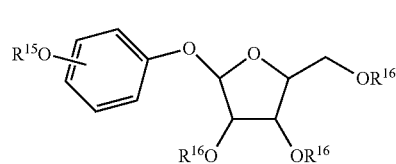

VII-C wherein:
$R^{15}$ is $C_1$-$C_4$ alkyl; and
$R^{16}$ represents independently for each occurrence —C(O)alkyl, —C(O)aryl, or —C(O)aralkyl.

In certain aspects, compound of formula VII-C is represented by:

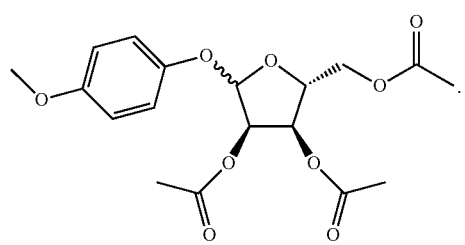 [SMILES: COc1ccc(OC2O[C@H](COC(C)=O)[C@@H](OC(C)=O)[C@H]2OC(C)=O)cc1]

In certain aspects, the acyl-deprotecting agent is a mixture of a base and a $C_1$-$C_6$ alcohol.

In certain aspects, the acyl-deprotecting agent is a mixture of $NH_3$ and MeOH.

In certain aspects, the method further comprises admixing a compound of formula VIII-C, an alkoxyphenol, and a Lewis acid to form the compound of formula VII-C, wherein formula VIII-C is represented by:

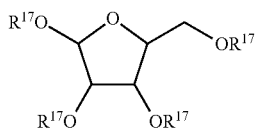

VIII-C wherein $R^{17}$ represents independently for each occurrence —C(O)alkyl, —C(O)aryl, or —C(O)aralkyl.

In certain aspects, compound of formula VIII-C is represented by:

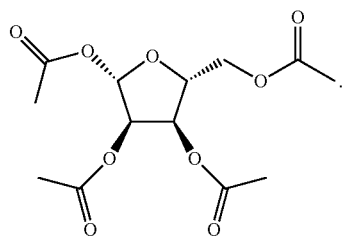 [SMILES: CC(=O)OC[C@H]1O[C@@H](OC(C)=O)[C@H](OC(C)=O)[C@@H]1OC(C)=O]

In certain aspects, the Lewis acid is $BF_3 \cdot OEt_2$.

Another aspect of the invention provides a method making an organophosphate compound, comprising admixing a compound of formula I-D and a compound of formula II-D to form a compound of formula III-D, wherein formula I-D is represented by:

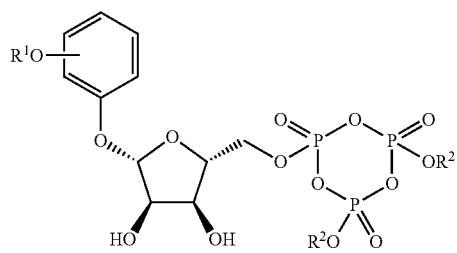

I-D wherein:

$R^1$ is $C_1$-$C_4$ alkyl;

$R^2$ represents independently for each occurrence H, an alkali metal, or $N(R^3)_4$; and $R^3$ represents independently for each occurrence H or $C_1$-$C_6$ alkyl;

formula II-D is represented by:

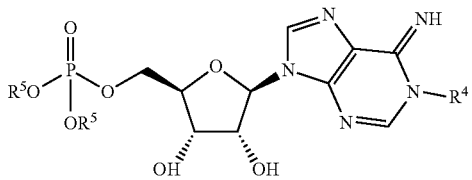

II-D wherein:

$R^4$ is $C_1$-$C_4$ alkyl;

$R^5$ represents independently for each occurrence H, an alkali metal, or $N(R^6)_4$; and $R^6$ represents independently for each occurrence H or $C_1$-$C_6$ alkyl; and formula III-D is represented by:

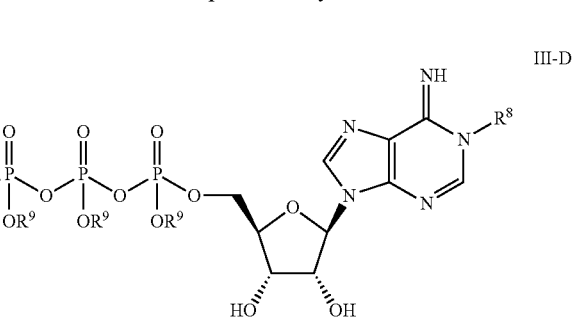

III-D wherein:

$R^7$ and $R^8$ are independently $C_1$-$C_4$ alkyl;

$R^9$ represents independently for each occurrence H, an alkali metal, or $N(R^{10})_4$; and $R^{10}$ represents independently for each occurrence H or $C_1$-$C_6$ alkyl.

In certain aspects, the Lewis acid is $ZnX_2$, wherein X is halogen.

In certain aspects, the method further comprises admixing a compound of formula IV-D and an alkylating agent to form said compound of formula II-D, wherein formula IV-D is represented by:

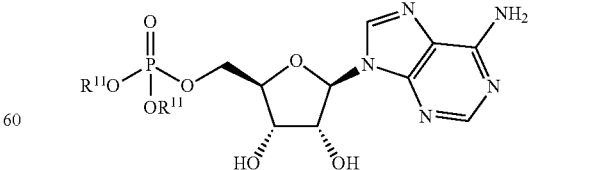

IV-D wherein $R^{11}$ represents independently for each occurrence H or an alkali metal.

In certain aspects, the alkylating agent is $SO_2(OR')_2$, wherein R' is $C_1$-$C_4$ alkyl.

In certain aspects, the method further comprises admixing a compound of formula V-D and a phosphorylating agent to form said compound of formula I-D, wherein formula V-D is represented by:

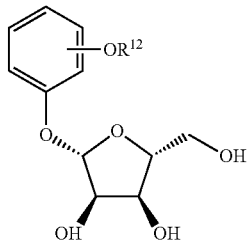

V-D wherein, $R^{12}$ is $C_1$-$C_4$ alkyl.

In certain aspects, the method comprises admixing said compound of formula V-D and $P(O)(OR')_3$ and then admixing $(OR'')_2P(O)OP(O)(OR'')_2$, wherein R' is $C_1$-$C_4$ alkyl, R'' is H or $N(R''')_4$, and R''' represents independently for each occurrence H or $C_1$-$C_4$ alkyl.

In certain aspects, the method further comprises admixing $P(O)X_3$, wherein X is a halogen.

In certain aspects, the method further comprises admixing $P(O)Cl_3$.

In certain aspects, the method further comprises hydrolyzing a compound of formula VI-D to form a compound of formula V-D, wherein formula VI-D is represented by:

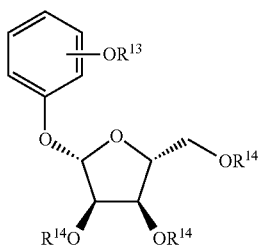

VI-D wherein:
$R^{13}$ is $C_1$-$C_4$ alkyl; and
$R^{14}$ represents independently for each occurrence —C(O)alkyl, —C(O)aryl, or —C(O)aralkyl.

In certain aspects, the method comprises admixing a base and a $C_1$-$C_6$ alcohol.

In certain aspects, the method further comprises admixing a compound of formula VII-D, a compound of formula VIII-D, and a Lewis acid to form said compound of formula VI-D, wherein formula VII-D is represented by:

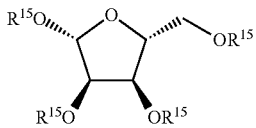

VII-D wherein $R^{15}$ represents independently for each occurrence —C(O)alkyl, —C(O)aryl, or —C(O)aralkyl; and formula VIII-D is represented by:

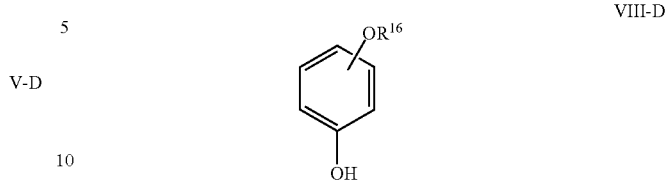

VIII-D wherein $R^{16}$ is $C_1$-$C_4$ alkyl.

Another aspect of the invention provides a method of making an organophosphate compound, comprising admixing a compound of formula I-E, a compound of formula II-E, and an oxidizing agent to form a compound of formula III-E, wherein formula I-E is represented by:

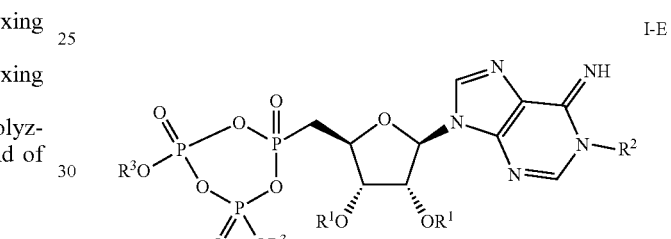

I-E wherein:

$R^1$ represents independently for each occurrence H, —C(O)alkyl, —C(O)aryl, or —C(O)aralkyl;

$R^2$ is $C_1$-$C_4$ alkyl;

$R^3$ represents independently for each occurrence H, an alkali metal, or $N(R^4)_4$; and $R^4$ represents independently for each occurrence H or $C_1$-$C_6$ alkyl;

formula II-E is represented by:

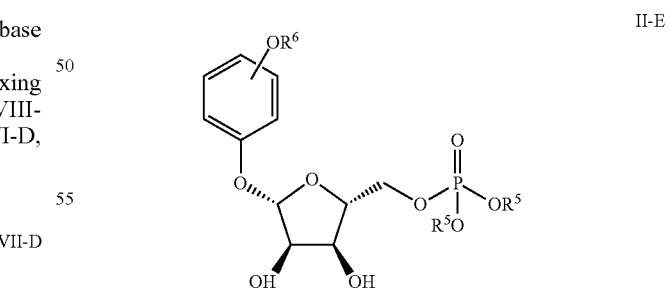

II-E wherein:

$R^5$ is $C_1$-$C_4$ alkyl;

$R^6$ represents independently for each occurrence H, an alkali metal, or $N(R^7)_4$; and $R^7$ represents independently for each occurrence H or $C_1$-$C_6$ alkyl; and formula III-E is represented by:

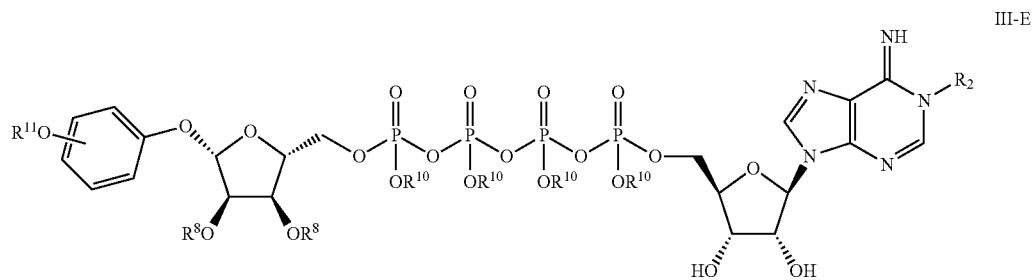

wherein:

$R^8$ represents independently for each occurrence H, —C(O)alkyl, —C(O)aryl, or —C(O)aralkyl;

$R^9$ and $R^{11}$ represent independently $C_1$-$C_4$ alkyl;

$R^{10}$ represents independently for each occurrence H, an alkali metal, or $N(R^{12})_4$; and $R^{12}$ represents independently for each occurrence H or $C_1$-$C_6$ alkyl.

In certain aspects, the method further comprises admixing a Lewis acid.

In certain aspects, the Lewis acid is $ZnCl_2$.

In certain aspects, the method further comprises admixing an acyl-deprotecting agent and said compound of formula III-E.

In certain aspects, the acyl-deprotecting agent is a base and $C_1$-$C_6$ alcohol.

In certain aspects, the method further comprises admixing a compound of formula IV-E and an oxidizing agent to form I-E, wherein formula IV-E is represented by

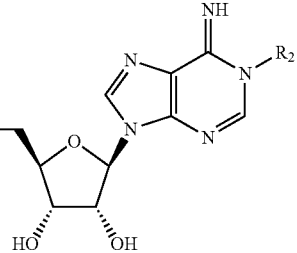

wherein:

$R^{13}$ is H, —C(O)alkyl, —C(O)aryl, or —C(O)aralkyl;

$R^{14}$ is $C_1$-$C_4$ alkyl;

$R^{15}$ represents independently for each occurrence H, an alkali metal, or $N(R^{16})_4$; and $R^{16}$ represents independently for each occurrence H or $C_1$-$C_6$ alkyl.

In certain aspects, the oxidizing agent is iodine.

In certain aspects, the method further comprises admixing a compound of formula V-E and a phosphorylating agent to form a compound of formula IV-E, wherein formula V-E is represented by:

V-E wherein:

$R^{17}$ is H, —C(O)alkyl, —C(O)aryl, or —C(O)aralkyl;

$R^{18}$ is $C_1$-$C_4$ alkyl; and $R^{19}$ and $R^{20}$ are independently alkyl, alkoxy, halogen, aryl, or aralkyl, or $R^{19}$ and $R^{20}$ taken with the aryl group to which they are attached, form a fused aromatic group.

In certain aspects, the phosphorylating agent is pyrophosphate.

In certain aspects, the method further comprises admixing a compound of formula VI-E and a compound of formula VII-E to form a compound of formula V-E, wherein formula VI-E is represented by:

VI-E wherein:

$R^{21}$ is H, —C(O)alkyl, —C(O)aryl, or —C(O)aralkyl; and $R^{22}$ is $C_1$-$C_4$ alkyl; and formula VII-E is represented by:

VII-E wherein:

$R^{23}$ and $R^{24}$ are independently alkyl, alkoxy, halogen, aryl, or aralkyl, or $R^{23}$ and $R^{24}$ taken with the aryl group to which they are attached, form a fused aromatic group.

In certain aspects, the method further comprises admixing a compound of formula VIII-E and an alkylating agent to form a compound of formula VI-E, wherein formula VIII-E is represented by:

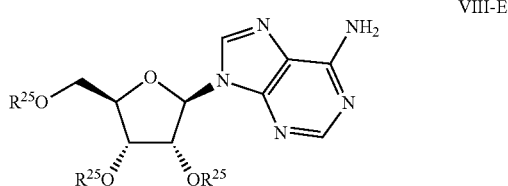

VIII-E wherein, $R^{25}$ is H, —C(O)CH$_3$, or —C(O)CH$_2$-phenyl.

In certain aspects, the alkylating agent is methyl iodide.

Another aspect of the invention provides a compound represented by the following formula:

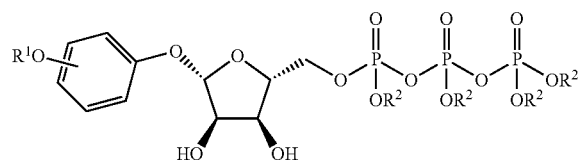

wherein:

$R^1$ is $C_1$-$C_4$ alkyl; and
$R^2$ represents independently for each occurrence H or an alkali metal.

Another aspect of the invention provides a compound represented by the following formula:

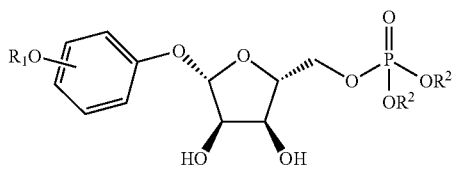

wherein:

$R_1$ is $C_1$-$C_4$ alkyl; and
$R^2$ represents independently for each occurrence H or an alkali metal; or two occurrences of $R^2$ taken together form an alkaline earth metal.

Another aspect of the invention provides a compound represented by the following formula:

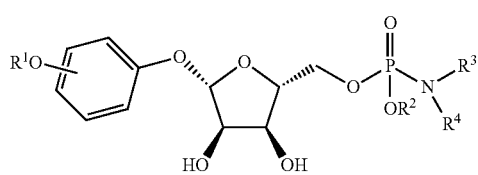

wherein:

$R^1$ is $C_1$-$C_4$ alkyl;
$R^2$ represents independently for each occurrence H or an alkali metal; and $R^3$ and $R^4$, taken together with the nitrogen atom to which they are attached, form a 3 to 6 membered heterocyclic ring.

DETAILED DESCRIPTION OF THE INVENTION

The present invention provides compounds and methods for making adenosine tetraphosphate compounds. It is contemplated that the organophosphate compounds modulate P2Y receptor activity, and thereby provide a therapeutic benefit to patients.

DEFINITIONS

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The term "including" is used to mean "including but not limited to". "Including" and "including but not limited to" are used interchangeably.

"P2Y receptor modulator" or "P2Y modulator" includes compounds having effect at the P2Y receptors, e.g., $P2Y_1$, $P2Y_2$, $P2Y_4$ or $P2Y_6$, particularly compounds having a modulating effect (increase or decrease) primarily at $P2Y_2$.

The term "Lewis acid" is art-recognized and generally refers to a compound or complex containing an element that is two electrons short of having a complete valence shell. Suitable Lewis acids include but are not limited to non-protic acids including metals, primarily halides and alkyl metal halides. Examples are manganese (II) chloride, stannic chloride, aluminium chloride, iron (III) chloride, boron trifluoride, niobium pentachloride, and lanthanide triflates such as ytterbium (III) triflate. Representative alkyl metal halides include MRX wherein R is an alkyl, preferably having 1 to 6 carbons, M is a metal, including but not limited to Group II metals, and X is a halide. In preferred embodiments, the Lewis acid is $SnCl_4$, $TiCl_4$, $ZnCl_2$, $AlCl_3$, $CuCl_2$, $FeCl_3$, or $BF_3.Et_2O$. In certain embodiments, the following Lewis acids are preferred: $MnCl_2$, $NiCl_2$, $ZnCl_2$, or $MgCl_2$.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

"Deprotecting agents" are reagents that remove protecting group from hydroxyl, amino or other functional groups. Hydroxyl protecting groups may be removed using various "deprotecting agents" known in the art, including those described in T. W. Greene, P. G. M. Wuts, "Protective Groups In Organic Synthesis," (J. Wiley & Sons, 1993). Examples of deprotecting agents include, but are not limited to, alcohols, hydroxide, acids, bases and amines. For alkanoyl protecting groups, such as acetyl, an example of a preferred deprotecting agent includes, but is not limited to a primary amine, such as n-propylamine. For aryl-alkyl-protecting groups, such as benzyl, examples of preferred deprotecting agents include, but are not limited to, hydrogenation using $H_2$ Pd/C; Na/t-BuOH; trifluoromethane sulfonic acid or TFA optionally in combination with PhSMe; $BF_3OEt_2$; or trimethylsilyliodide (TMSI). Solvent can also be used as deprotecting agent, such as water, methanol, ethanol, or combinations thereof. The term "acyl deprotecting" agent refers to a deprotecting agent that can convert an acyl group to a hydroxyl group.

The term "leaving group" refers to a functionality which upon bond cleavage departs with an electron pair. In general, good leaving groups are those moieties which are expelled from the substrate as weak bases. For example, sulfates, sulfonates, chloride, bromide, iodide, phosphates and the like are good leaving groups. In addition, some moieties may be good leaving groups when protonated or complexed with a Lewis acid. For example, alkoxide ions are generally poor leaving groups, but alcohols are good leaving groups. It should be noted that ring strain may, in some cases, allow a rather poor leaving group to be expelled, as in the case of epoxides, aziridines, and the like.

"Alkyl" includes saturated aliphatic groups, e.g., straight-chain alkyl groups such as methyl, ethyl, propyl, butyl, pentyl, hexyl, heptyl, octyl, nonyl, and decyl; branched-chain alkyl groups (e.g., isopropyl, tert-butyl, and isobutyl); cycloalkyl (alicyclic) groups like cyclopropyl, cyclopentyl, cyclohexyl, cycloheptyl, and cyclooctyl); lower alkyl-substituted cycloalkyl groups; and cycloalkyl-substituted alkyl groups. In an embodiment, alicyclic rings do not include bridged rings.

"Alkyl" groups may also optionally include heteroatoms, i.e., where oxygen, nitrogen, sulfur or phosphorus atoms replaces one or more hydrocarbon backbone carbon atoms, particularly where the substitution does not adversely impact the efficacy of the resulting compound.

Straight or branched alkyl groups may have six or fewer carbon atoms in their backbone (e.g., C1-C6 for straight chain, C3-C6 for branched chain), and more preferably four or fewer. Preferred cycloalkyl groups have from three to eight carbon atoms in their ring structure, and more preferably five or six carbons in the ring structure. "C1-C6" includes alkyl groups containing one to six carbon atoms.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

The term "aryl" is art-recognized and includes 5-, 6- and 7-membered single-ring aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl. The aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "alkylaryl" or an "aralkyl" moiety is an alkyl substituted with an aryl group (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl groups such as cyclopropenyl, cyclopentenyl, cyclohexenyl, cycloheptenyl, and cyclooctenyl; alkyl or alkenyl-substituted cycloalkenyl groups, and cycloalkyl or cycloalkenyl-substituted alkenyl groups.

"Alkenyl" groups may also optionally include heteroatoms, i.e., where oxygen, nitrogen, sulfur or phosphorus atoms replaces one or more hydrocarbon backbone carbon atoms, particularly where the substitution does not adversely impact the efficacy of the resulting compound.

Straight or branched alkenyl groups may have six or fewer carbon atoms in their backbone (e.g., C2-C6 for straight chain, C3-C6 for branched chain.) Preferred cycloalkenyl groups have from three to eight carbon atoms in their ring structure, and more preferably have five or six carbons in the ring structure. The term "C2-C6" includes alkenyl groups containing two to six carbon atoms.

"Substituted alkenyls" refers to alkenyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups.

"Alkynyl" groups may also optionally include heteroatoms, i.e., where oxygen, nitrogen, sulfur or phosphorus atoms replaces one or more hydrocarbon backbone carbon atoms, particularly where the substitution does not adversely impact the efficacy of the resulting compound Straight or branched chain alkynyls group may have six or fewer carbon atoms in their backbone (e.g., C2-C6 for straight chain, C3-C6 for branched chain). The term "C2-C6" includes alkynyl groups containing two to six carbon atoms.

"Substituted alkynyls" refers to alkynyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have corresponding chain lengths, e.g., 2-5 carbon atoms.

"Acyl" includes compounds and moieties which contain the acyl radical (CH3CO—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "oxo" refers to a "O=" substituent. For example, a cyclohexanone is a cyclohexane bearing an oxo group.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named.

"Alkoxyalkyl" includes moieties where an alkoxy group is bonded to an alkyl group; "alkoxyaryl", "thioalkoxyalkyl", "alkylaminoalkyl" and "alkylthioalkyl" are analogously named.

"Alkoxy" includes alkyl, alkenyl, and alkynyl groups covalently linked to an oxygen atom. Examples of alkoxy groups include methoxy, ethoxy, isopropyloxy, propoxy, butoxy, and pentoxy groups. Examples of "substituted alkoxy" groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy. In a preferred embodiment, the "alkoxy" group is an alkyl group covalently linked to an oxygen atom.

The terms "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In an embodiment, heterocyclic rings do not include bridged rings.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" is art recognized and refers to —OH.

The term "halogen" includes fluorine, bromine, chlorine, iodine, etc. The term "perhalogenated" generally refers to a moiety wherein all hydrogens are replaced by halogen atoms.

The terms "amine" and "amino" are art-recognized and refer to both unsubstituted and substituted amines, e.g., a moiety that may be represented by the general formulas:

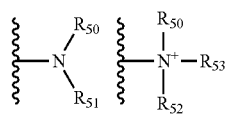

wherein $R_{50}$, $R_{51}$ and $R_{52}$ each independently represent a hydrogen, an alkyl, an alkenyl, —$(CH_2)_m$—$R_{61}$, or $R_{50}$ and $R_{51}$, taken together with the N atom to which they are attached complete a heterocycle having from 4 to 8 atoms in the ring structure; $R_{61}$ represents an aryl, a cycloalkyl, a cycloalkenyl, a heterocycle or a polycycle; and m is zero or an integer in the range of 1 to 8.

The term "imino" is art-recognized and may be represented by the general formula:

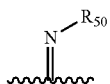

wherein $R_{50}$ is H, alkyl, aryl, or aralkyl.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Selective" means that a compound binds to or inhibits a certain P2Y receptor with greater affinity or potency, respectively, compared to at least one other receptors, or preferably compared to all other receptors of the same class (e.g., all the P2Y receptors). In some embodiments, the compounds of the invention have binding or inhibition selectivity for P2Y2 over any other P2Y receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23).

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF3, —CN, or the like.

Methods of Making P2Y Receptor Modulators

The invention provides methods of making organophosphate compounds, such as those represented by Formulae A, B, C, and D, including salts thereof:

Formula A

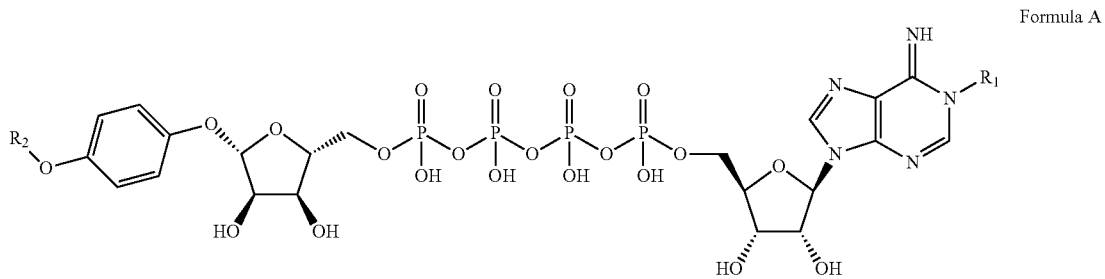

wherein, $R_1$ is H, $C_1$-$C_4$ alkyl or cycloalkyl; and $R_2$ is H or $C_1$-$C_4$ alkyl.

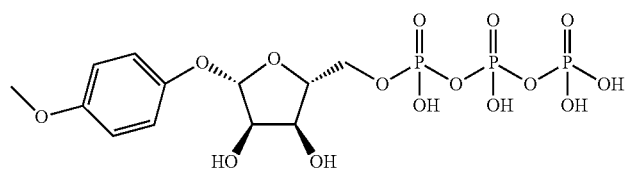

Formula B

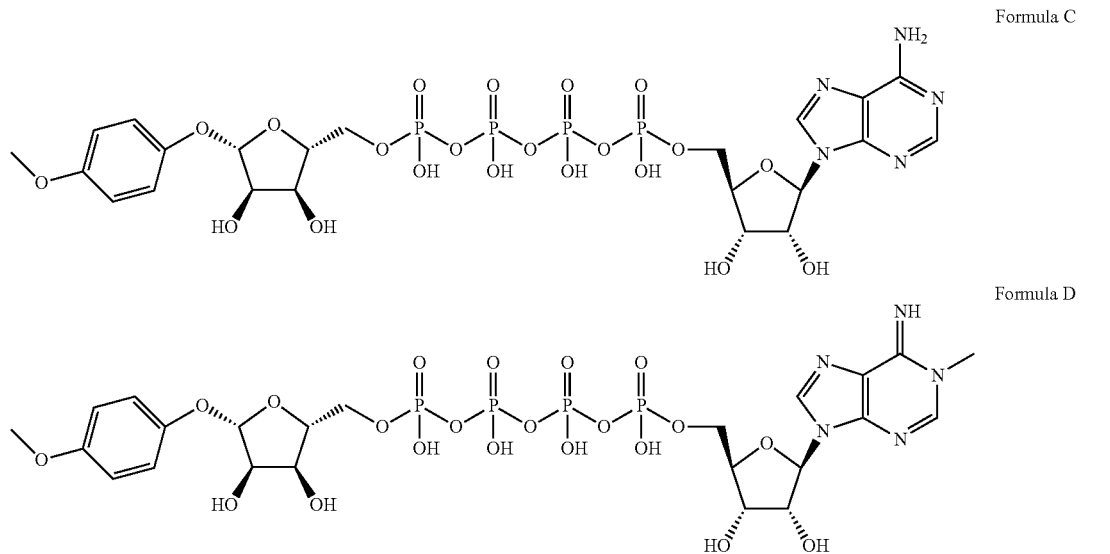

Formula C

Formula D

Method-I

Organophosphate compounds of formula A can be prepared based on the synthetic procedure outlined below. The synthesis of compound B (Scheme I) can be carried out through a four step-sequence. Suitable starting materials for this sequence include 1,2,3,5-tetra-O-acetyl-β-D-ribofuranose and 4-methoxyphenol, noting that the hydroxyl groups of the ribose sugar can be protected using a variety of protecting groups known in the art. The synthesis begins by reacting the alkoxyphenol with the ribofuranose in presence of a Lewis acid. In the next step, the hydroxyl groups of the ribose moiety are deprotected by basic hydrolysis or by another suitable deprotecting agent. Following deprotection, the phosphate group is installed at the $C_5$ position of the ribose ring by reacting 4-methoxyphenyl-β-D-ribofuranoside with a phosphate donor to form intermediate E. Finally, the organo-monophosphate compound is reacted with pyrophosphoric acid to form compound B.

Scheme I.

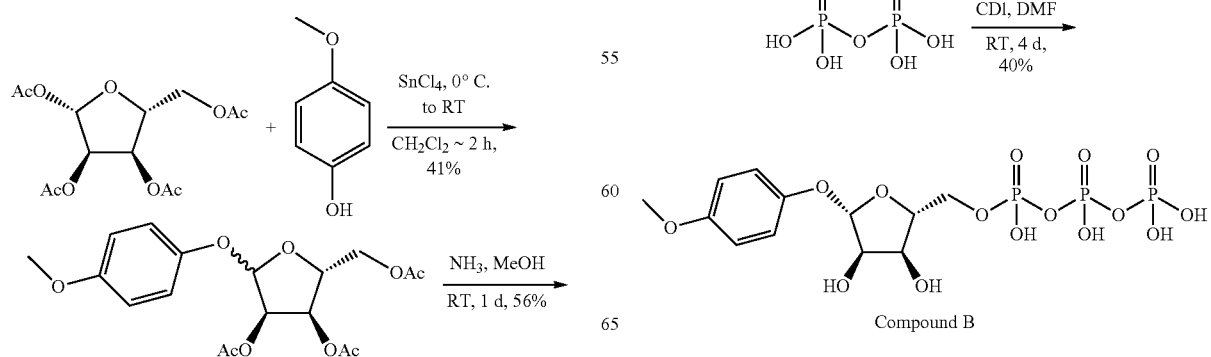

-continued

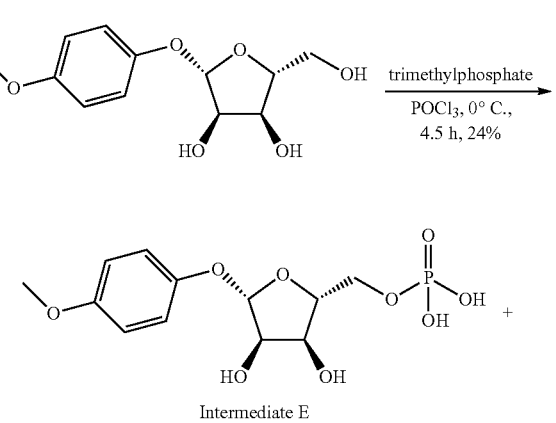

Intermediate E

Compound B

The synthesis of intermediate F can be carried out through a single-step reaction as shown in Scheme II. Adenosine-5'-monophosphate is reacted with imidazole in the presence of a base to form adenosine-5'-phosphorimidazolate (intermediate F).

Scheme II.

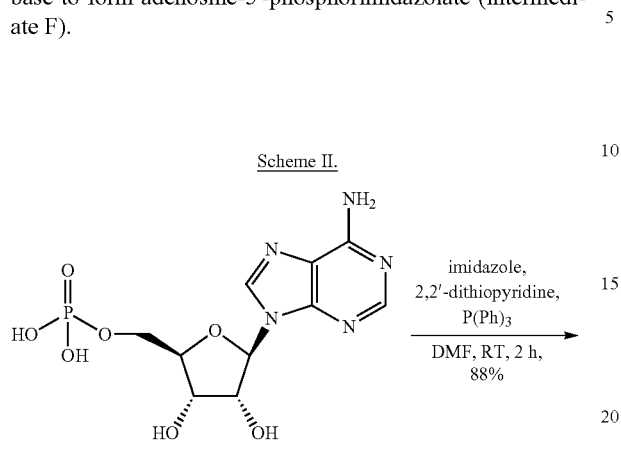

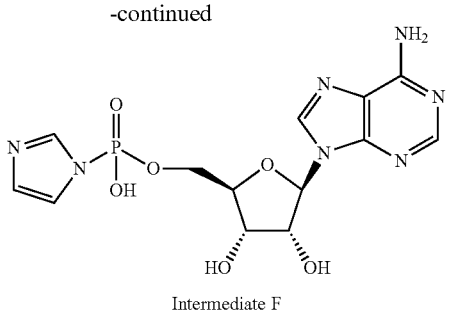

Intermediate F

The next phase of the synthesis involves coupling compound B and intermediate F in the presence of a Lewis acid to form compound C. Then, compound C is treated with an alkylating agent to form compound D as shown in Scheme III.

Scheme III.

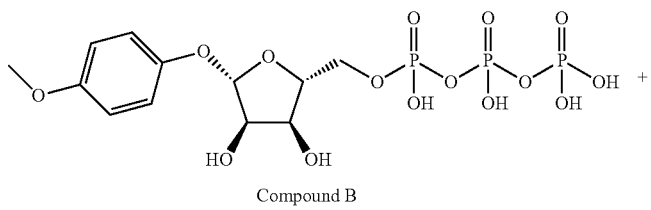

Compound B

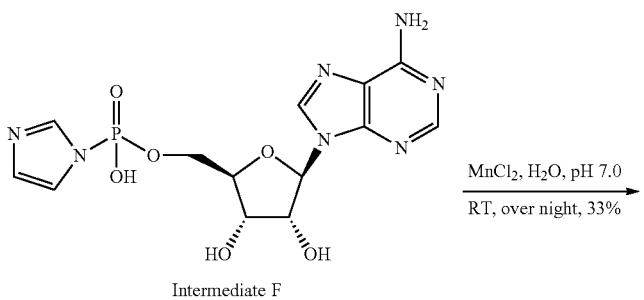

Intermediate F

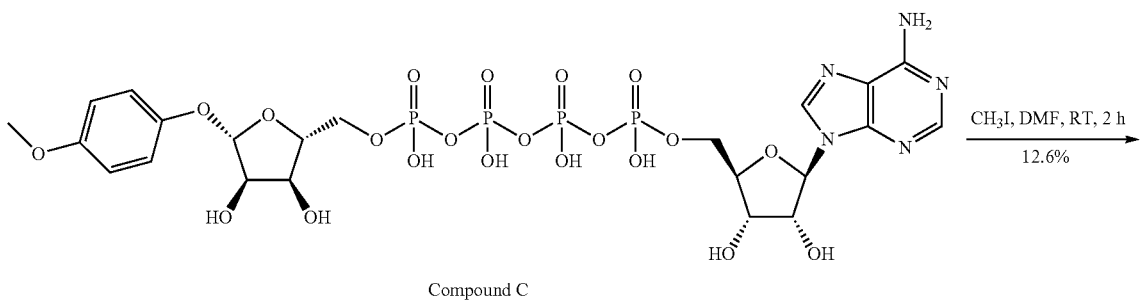

Compound C

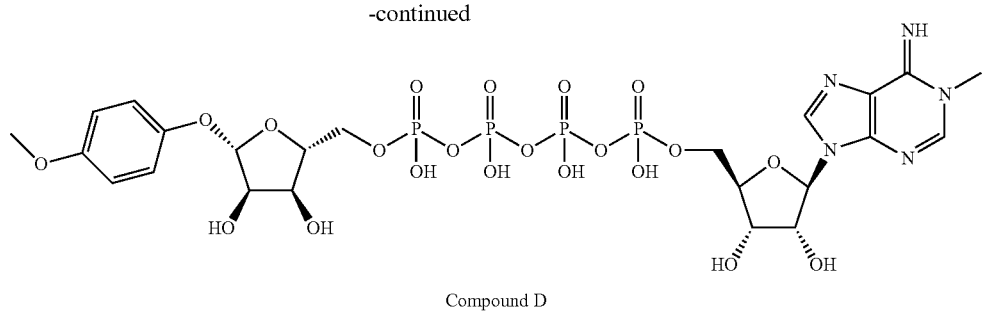

Compound D

Method-II

Organophosphate compounds of formula A can be prepared based on an alternative synthetic procedure outlined below. Suitable starting materials for this sequence include 1,2,3,5-tetra-O-acetyl-β-D-ribofuranose and 4-methoxyphenol. Similar to Method-I, synthesis of the organo-monphosphate compound (intermediate E) is carried out according to Scheme IV. In the presence of a Lewis acid, 4-methoxyphenol is attached to the ribose sugar. In the next step, the hydroxyl groups of the ribose moiety are deprotected by basic hydrolysis or by another suitable deprotecting agent. Following deprotection, the phosphate group is installed at the $C_5$ position of the ribose ring by reacting 4-methoxyphenyl-β-D-ribofuranoside with a phosphate donor to form intermediate E.

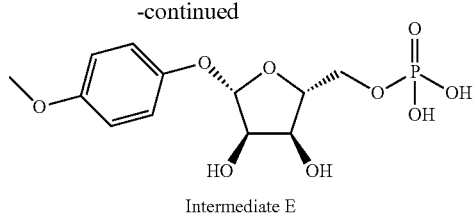

Intermediate E

Next, ATP-imidazolate is prepared by treating ATP with imidazole in the presence of a base.

Scheme IV.

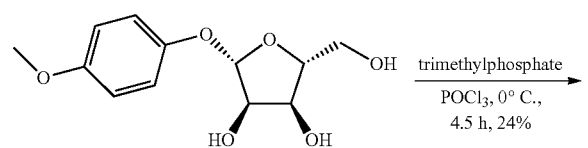

Scheme V.

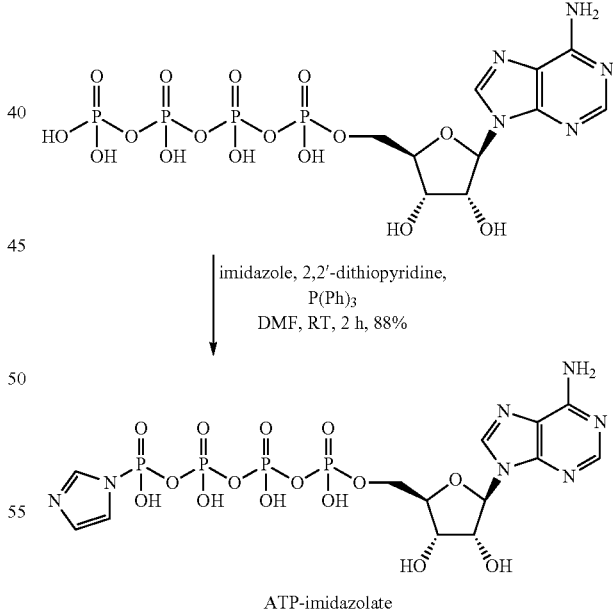

ATP-imidazolate

Finally, intermediate E and the ATP-imidazolate undergo a coupling reaction in the presence of a Lewis acid to form compound C. Then, compound C is treated with an alkylating agent to form compound D as shown in Scheme VI.

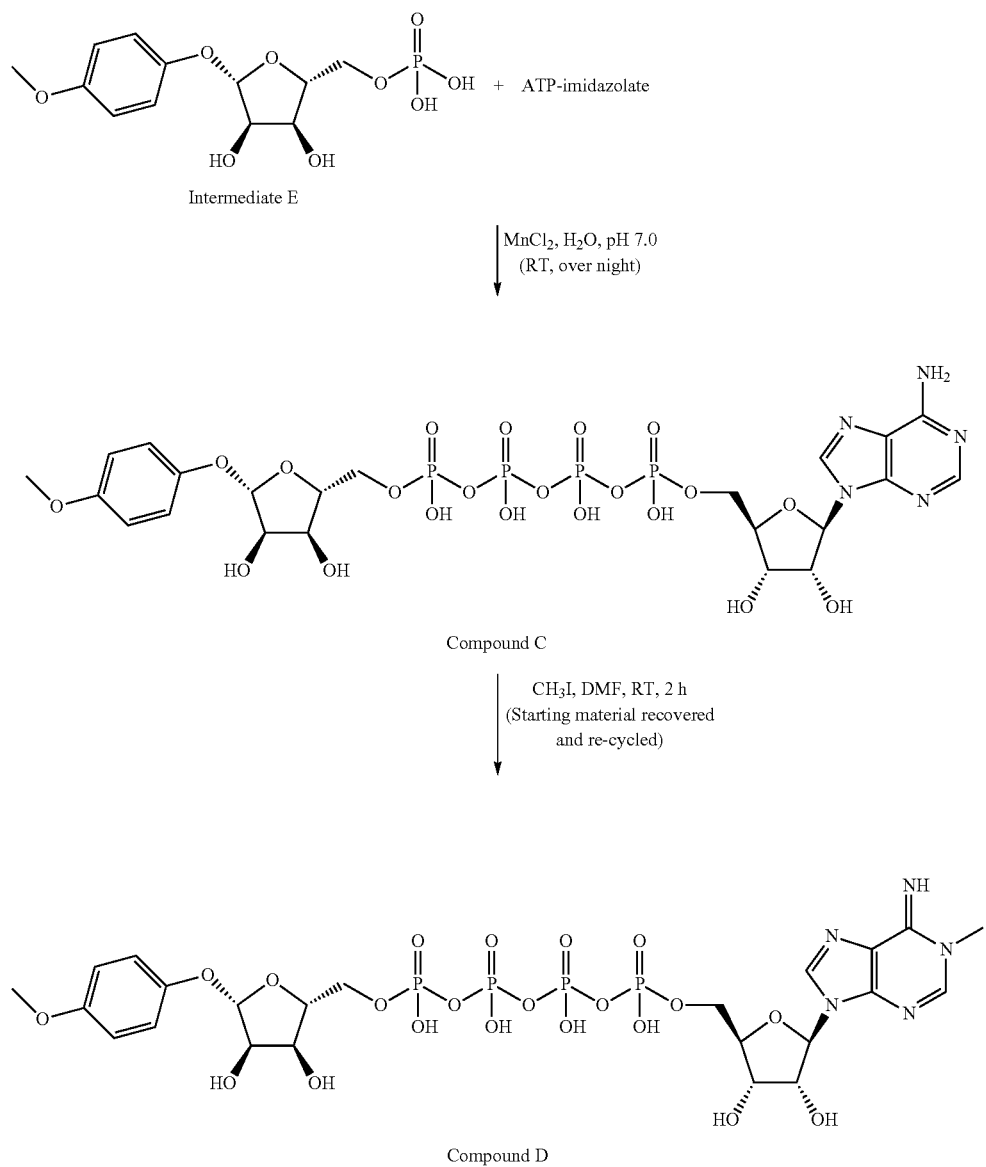

Scheme VI.

Method-III

Organophosphate compounds of formula A can be prepared based on another alternative synthetic procedure outlined below. Analogous to the previous methods, intermediate E is prepared by a sequence of reactions as shown in Scheme VII. Suitable starting materials for this sequence include 1,2,3,5-tetra-O-acetyl-β-D-ribofuranose and 4-methoxyphenol, noting that the hydroxyl groups of the ribose sugar can be protected using other protecting groups. The synthesis begins by reacting the alkoxyphenol with the ribofuranose in the presence of a Lewis acid. In the next step, the hydroxyl groups of ribose moiety are deprotected by basic hydrolysis or by another suitable deprotecting agent. Following deprotection, the phosphate group is installed at the $C_5$ position of the ribose ring by reacting 4-methoxyphenyl-β-D-ribofuranoside with a phosphate donor to form intermediate E.

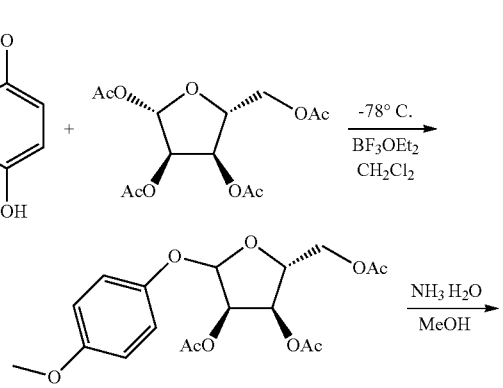

Scheme VII.

Scheme VIII.

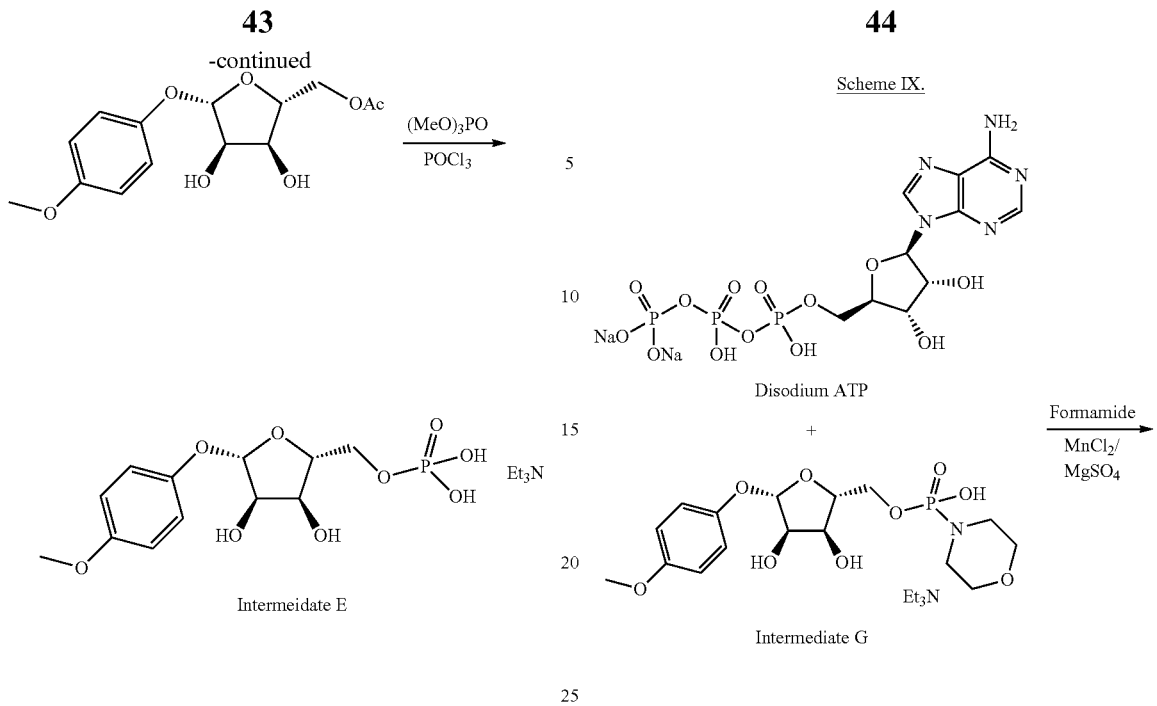

The next stage of the synthesis involves attaching a morpholine group to intermediate E to form intermediate G as shown in Scheme VIII.

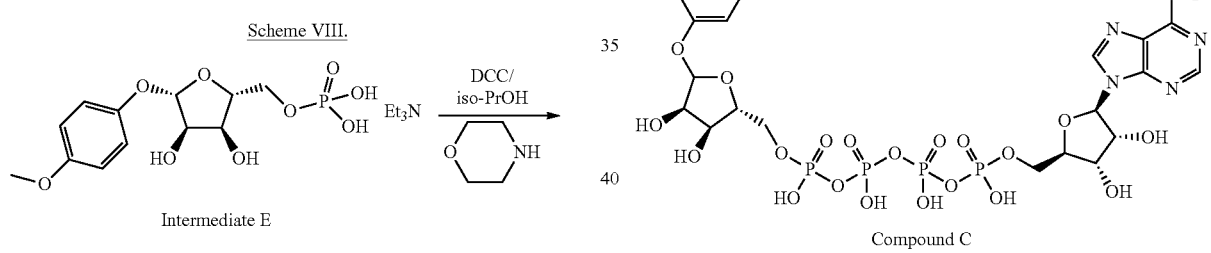

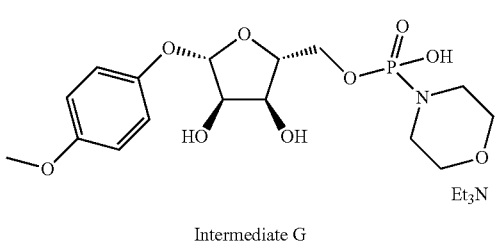

Finally, intermediate G and disodium ATP undergo a coupling reaction in the presence of a Lewis acid to form compound C shown in Scheme IX. Then, compound C is treated with an alkylating agent such as methyl iodide to form compound D.

Method-IV

It is contemplated that organophosphate compounds of formula A may be prepared based on another alternative synthetic procedure outlined below. According to this method, organophosphate intermediate H is prepared by a sequence of reactions as shown in Scheme X. It is contemplated that suitable starting materials for this sequence include (2S,3R,4R,5R)-2-acetoxy-5-(benzoyloxymethyl)tetrahydrofuran-3,4-diyl dibenzoate and 4-methoxyphenol, noting that the hydroxyl groups of the ribose sugar may be protected using other protecting groups. The synthesis begins by reacting the protected tetrahydrofuran with the alkoxyphenol under Vorbruggen conditions, which entails performing the reaction in the presence of a Lewis acid. Additional procedures for carrying out coupling reactions using Vorbruggen conditions can be found in U. Niedballa, H. Vorbruggen, *Angew. Chem. Int. Ed.* 1970, 9, 461; Vorbruggen et al., *Ber.* 1981, 114, 1234, and H. Vorbruggen et al. *Ber.* 1981, 114, 1256, each of which is hereby incorporated by reference. In the next step, the hydroxyl groups of the ribose moiety are deprotected by basic hydrolysis or by another suitable deprotecting agent. Following deprotection, the phosphate group is installed at the $C_5$-position of the ribose ring by reacting 4-methoxyphenyl-β-D-ribofuranoside with a phosphate donor to form intermediate H.

Scheme X.

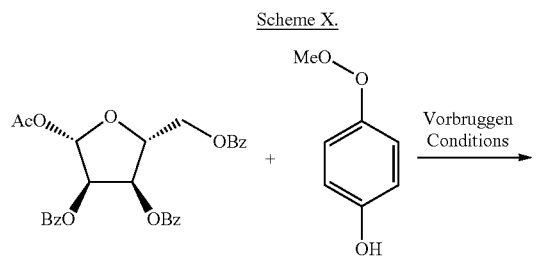

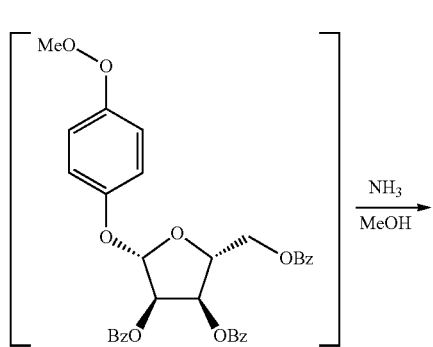

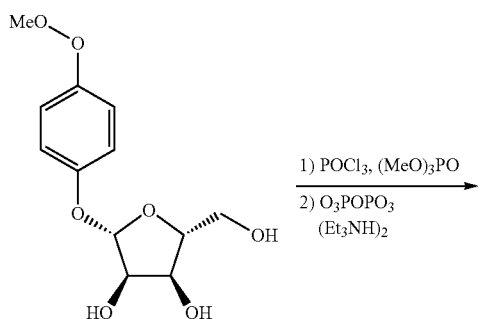

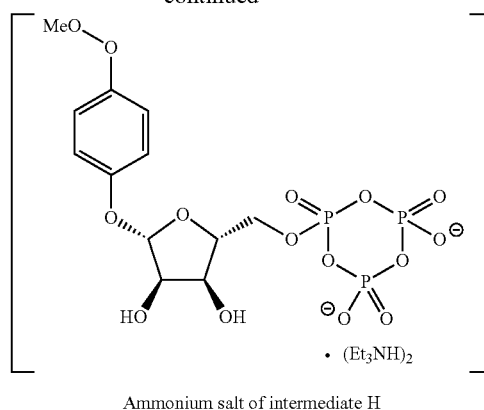

Ammonium salt of intermediate H

In the next stage, 5'-adenosine monophosphate is reacted with a methylating agent to form intermediate J under acidic conditions. One suitable methylating agent is dimethyl sulfate.

Scheme XI.

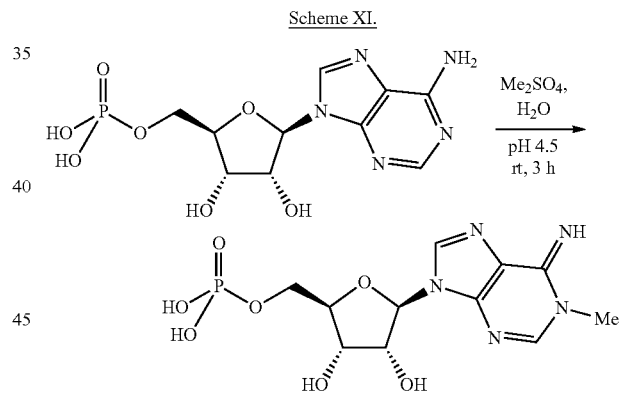

Intermediate J

Finally, it is contemplated that intermediates J and H will undergo a coupling reaction in the presence of a Lewis acid to form compound D as shown in Scheme XII. It is contemplated that the product of the coupling reaction may be purified using cation-exchange chromatography. Additionally, it is contemplated that the product may be purified using reverse phase high performance chromatography. Of course, other suitable methods of purifying the compound would be appreciated by one of ordinary skill in the art.

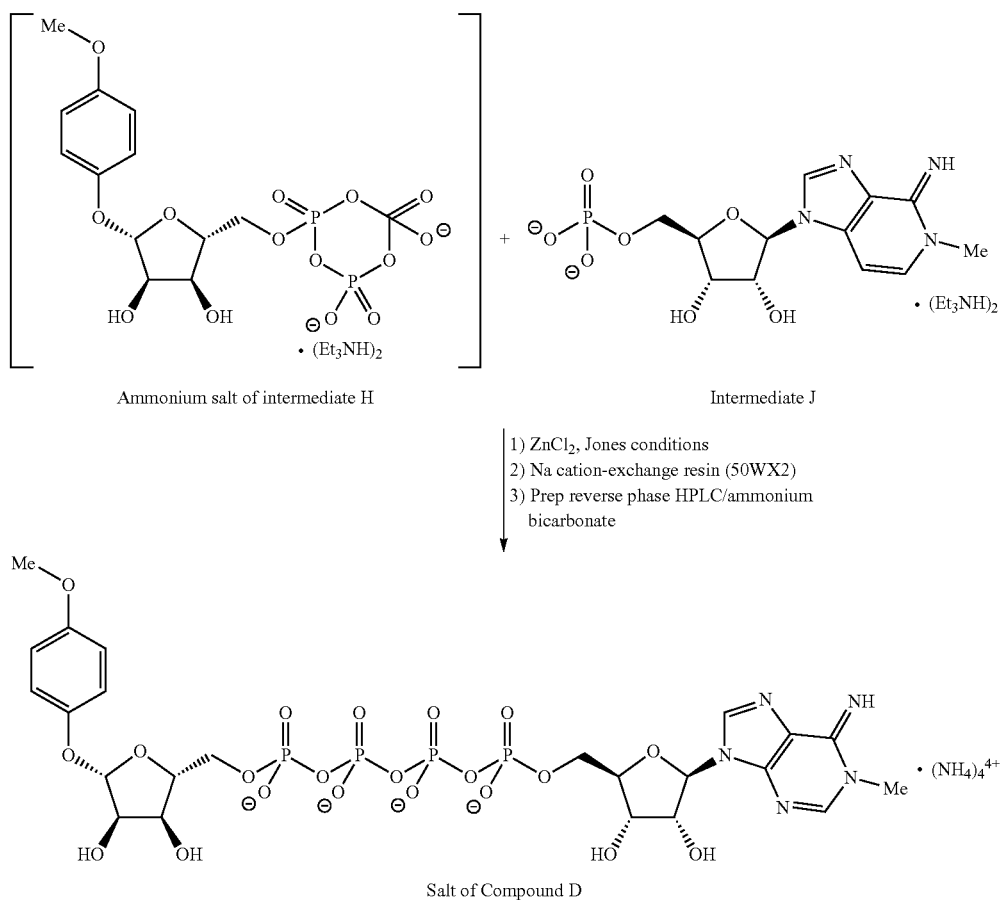

Scheme XII.

Ammonium salt of intermediate H        Intermediate J

1) ZnCl$_2$, Jones conditions
2) Na cation-exchange resin (50WX2)
3) Prep reverse phase HPLC/ammonium bicarbonate Salt of Compound D Method-V It is contemplated that organophosphate compounds of formula A can be prepared based on another synthetic procedure as outlined below. In the first stage, analogous to methods above, intermediate E is to be prepared from ribose. In the next stage, intermediate I is to be prepared by a sequence of reactions as shown in Scheme XIII. (2R,3R,4R,5R)-2-(6-amino-9H-purin-9-yl)-5-(hydroxymethyl)tetrahydrofuran-3,4-diyl diacetate is methylated by an alkylating agent such as methyl iodide. Next, the alkylated product is reacted with salicyl chlorophosphite. The salicyl phosphate group binds at the C$_5$ carbon of the ribose sugar. This compound is further phosphorylated in the presence of pyrophosphate. This phosphorylated compound is then treated with iodine to form intermediate I.

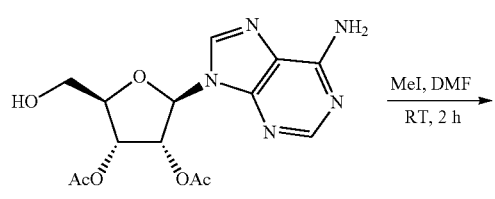

Scheme XIII.

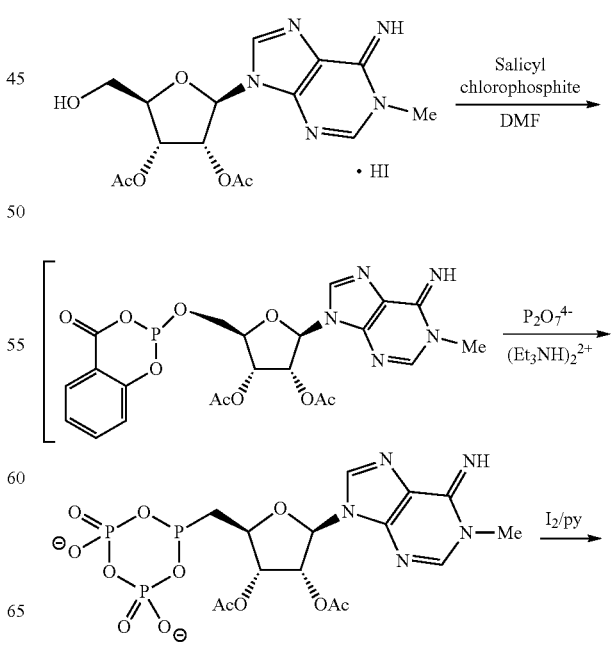

-continued

-continued

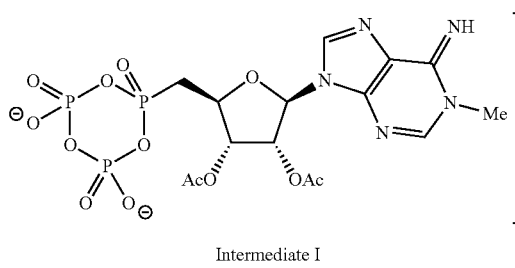

Intermediate I

In the next step, intermediate I and intermediate E undergo a coupling reaction in the presence of a Lewis acid and an oxidizing agent to form a tetraphosphate compound. Then, the tetraphosphate product is treated with an acyl-deprotecting agent to remove the acetyl groups, providing compound D as shown in Scheme XIV. It is contemplated that the product from the deprotection reaction may be purified using cation-exchange chromatography. Additionally, the product may be purified using reverse phase high performance chromatography. Of course, other suitable methods of purifying the compound would be appreciated by one of ordinary skill in the art The methods described above are provided for the purpose of illustrating the invention, and are not to be construed as limiting the scope or spirit of the invention. Furthermore, additional compounds and synthetic procedures are described in International Patent Application No. PCT/US2007/24150, which is hereby incorporated by reference in its entirety.

EXAMPLES

The invention now being generally described, will be more readily understood by reference to the following examples, which are included merely for purposes of illustrating certain aspects and embodiments of the present invention, and are not intended to limit the invention.

EXAMPLE 1

Preparation of 4-Methoxyphenyl(tri-o-acetyl-α,β-D-ribofuranoside)

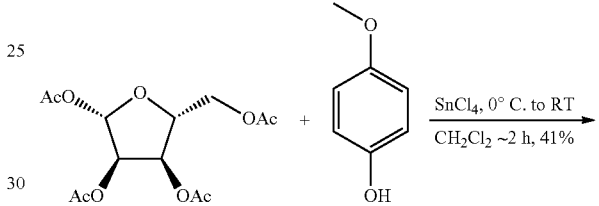

Scheme XIV.

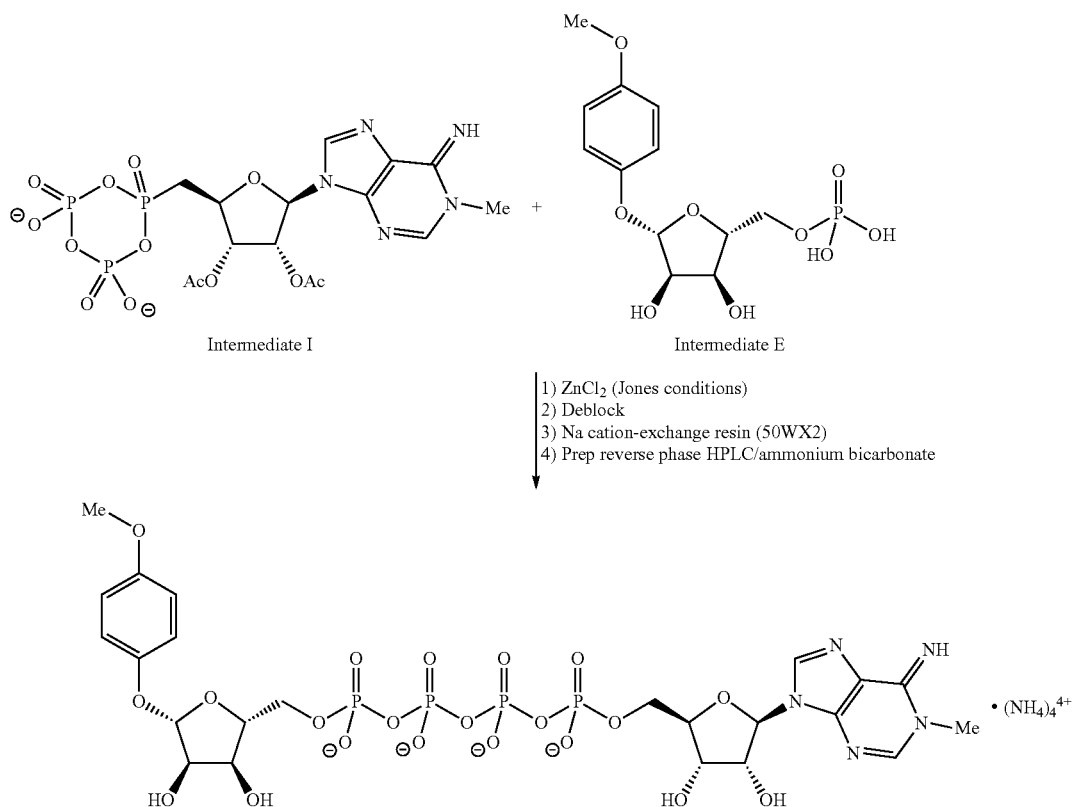

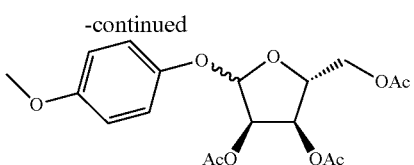

1,2,3,5-tetra-O-acetyl-β-D-ribofuranose (2.2 g, 7 mmol) was dissolved in 30 mL CH$_2$Cl$_2$. The solution was treated at 0° C. with SnCl$_4$ (850 μL, 7 mmol) in 3 mL CH$_2$Cl$_2$. After 15 min, dried 4-methoxyphenol (1 g, 8 mmol) was added and the suspension was treated for approximately 1 minute in ultrasonic bath until the mixture became homogenous. The mixture was stirred at 0° C. for 10 minutes. The cooling bath was removed, stirring was continued for 40 minutes and the mixture was allowed to reach room temperature. Stirring was continued for additional 1 hour. The reaction mixture was poured into a saturated solution of NaHCO$_3$ (40 ml, 0° C.) and extracted with CHCl$_3$ (2×50 ml). The combined organic extracts (white emulsion) were co-evaporated with ethanol (3×100 ml) to dryness. The yellow residue was suspended in CHCl$_3$ and applied to a column of silica gel. Elution with CHCl$_3$-EtOH, gradient (98:2 to 90:10) and evaporation of the appropriate fractions gave an anomeric mixture of the title compound as yellow oil (1.1 g, 2.9 mmol, 41%).

EXAMPLE 2

Preparation of 4-methoxyphenyl-β-D-ribofuranoside

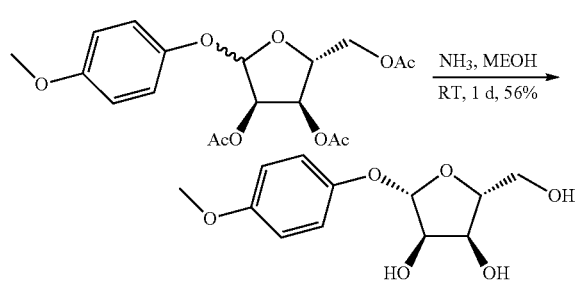

4-Methoxyphenyl(tri-O-acetyl-α,β-D-ribofuranoside) (1 g, 2.65 mmol) was dissolved in 20 ml methanol and treated with a solution of NH$_3$ (25%, 5 ml). After 24 hour at room temperature the residue was co-evaporated with water (2×50 ml) and ethanol (2×50 ml). The resulting yellow oil was dissolved in 20 ml toluene-methanol (4:1) and applied to a column of silica gel and the product was eluted with toluene-methanol (4:1). Evaporation of the product fractions gave the 4-methoxyphenyl-α,β-D-ribofuranoside as white solid (510 mg). This material gave on the TLC a single spot. The α and β anomers were separated by preparative RP-HPLC and yielded 380 mg (1.48 mmol, 56%) of the 4-methoxyphenyl-β-D-ribofuranoside and 95 mg (0.37 mmol) of the 4-methoxyphenyl-α-D-ribofuranoside. MS (ESI): m/z 279.2 (M+23)$^+$.

EXAMPLE 3

Preparation of 4-Methoxyphenyl-β-D-ribofuranosid-5'-monophosphate

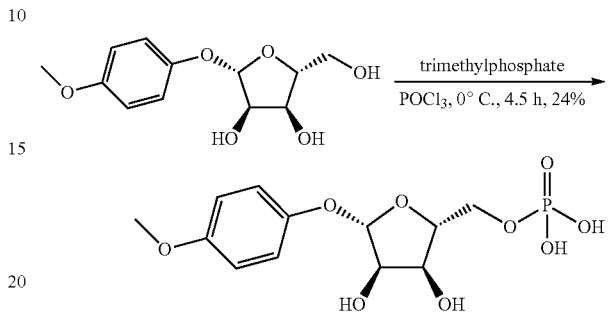

4-Methoxyphenyl-β-D-ribofuranoside (890 mg, 3.47 mmol) was dissolved in 18 ml trimethylphosphate under argon atmosphere. The solution was cooled to 0° C. and after 10 minutes, 412 μl (4.52 mmol) phosphorus oxychloride were carefully added. After 4.5 hours, excess of POCl$_3$ was removed in vacuo within 10 minutes. The remaining solution of the initially formed intermediate dichlorophosphate was then quenched by adding 30 ml of 1M triethylammonium bicarbonate buffer (pH 7.5) at 0° C. Purification by ion exchange chromatography gave the product (0.8 mmol, 24%) as triethylammonium salt, which was subsequently used in the next step without further purification. MS (ES) m/z 335 [M-H]$^-$.

EXAMPLE 4

Preparation of 4-Methoxyphenyl-β-D-ribofuranosid-5'-triphosphate

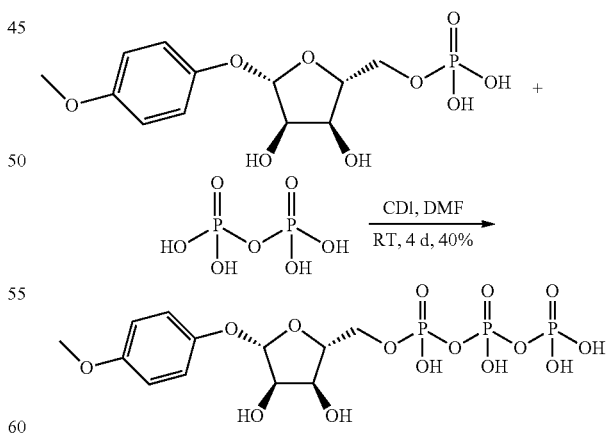

4-Methoxyphenyl-β-D-ribofuranosid-5'-monophosphate, triethylammonium salt (0.8 mmol) was dissolved in methanol (20 ml) and treated with tri-n-butylamine (850 μl, 2.4 mmol). The solution was evaporated to dryness, dissolved in methanol and re-evaporated twice. Subsequently, this procedure was repeated three times with anhydrous DMF (15 ml) using an oil pump. The residue was dissolved in 12 ml anhydrous DMF, N,N'-carbonyldiimidazole (CDI) (1.3 g, 8 mmol) was added and the mixture was stirred 1.5 h at room temperature. After the excess amount of CDI was degraded by addition of dry methanol (526 µl, 13 mmol), pyrophosphoric acid, tri-n-butylammonium salt (5.5 mmol) in dry DMF (10 ml) was added and the resulting suspension was stirred at room temperature. The progress of the reaction was monitored by HPLC. After 4 days the reaction mixture was diluted to 2000 ml, and the pH adjusted to 7.5. Purification by ion exchange chromatography yielded the product as its triethylammonium salt, which was subsequently precipitated as its sodium salt (180 mg, 0.32 mmol, 40%). MS (ES): m/z 495 [M-H]$^-$, 598 [M+C$_6$H$_{15}$N]$^+$.

EXAMPLE 5

Preparation of Adenosine-5'-phosphoroimidazolate

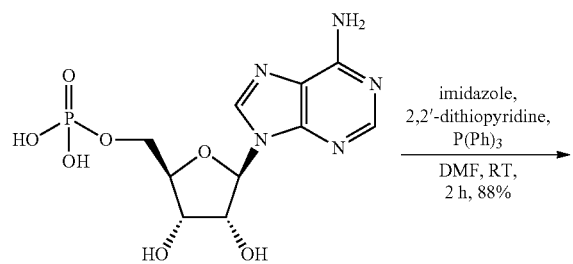

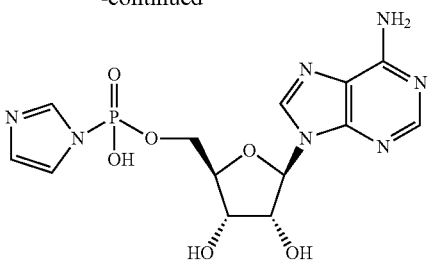

Adenosine-5'-monophosphate, free acid (6 mmol) was dissolved in 1:1 mixture of methanol and water (100 ml) and the resulting solution was treated with tri-n-butylamine (7.2 ml, 30 mmol). The solution was evaporated to dryness, dissolved in methanol and re-evaporated twice. Subsequently, this procedure was repeated twice with anhydrous DMF (50 ml) using an oil pump. The residue was dissolved in 30 ml anhydrous DMF, imidazole (4.1 g, 60 mmol) 2,2'-dithiopyridine (10.6 g, 48 mmol) and triphenylphosphine (12.6 g, 48 mmol) were added and the solution was stirred for 2 hours at room temperature. The solution was treated with 10 ml of a 1M sodium perchlorate solution in acetone and 30 ml acetone. The sodium salt of adenosine-5'-phosphoroimidazolate was obtained as white precipitate, which was collected by centrifugation, washed with acetone (5×30 ml) and dried in a desiccator. The product (2.25 g, 5.3 mmol, 88%) was used in the next step without further purification.

EXAMPLE 6

Preparation of Intermediate C

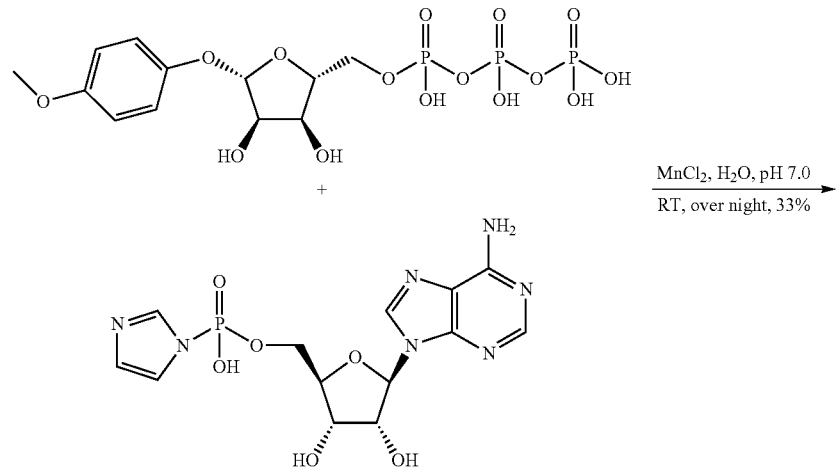

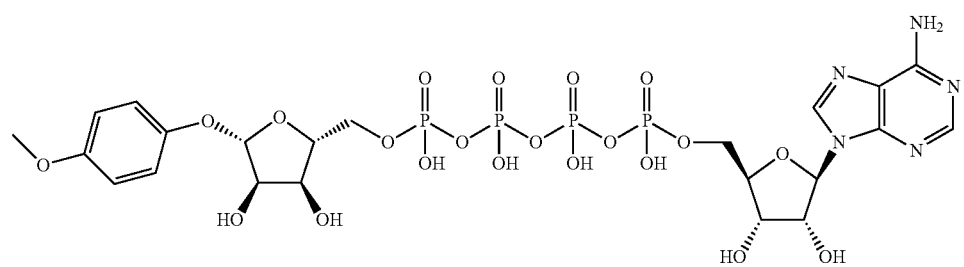

4-Methoxyphenyl-β-D-ribofuranosid-5'-triphosphate, sodium salt, (478 mg, 0.85 mmol) was dissolved in water (3 ml) and MnCl$_2$×2H$_2$O (688 mg, 4.25 mmol) was added. The resulting solution was slowly added to a solution of adenosine-5'-phosphorimidazolate (1.8 g, 4.25 mmol) in 0.2 M N-ethylmorpholine-HCl buffer pH 7.0 (7 ml). The suspension (pH 4.5) was treated carefully with a 2 M HCl solution until the precipitation dissolved almost completely (pH 2.8). The reaction mixture was stirred over night at room temperature. The reaction mixture was then treated with a 1M versenol solution until the suspension became clear. Subsequently, it was diluted to 2000 ml, the pH adjusted to 7.5 and the solution applied to an ion exchange chromatography column. The fractions containing the product were pooled and the product was isolated as triethylammonium salt (335 mg, 0.28 mmol, 33%), which was used in the next step without further purification. MS (ES) m/z 824 [M-H]$^-$.

Compound C, triethylammonium salt (335 mg, 0.28 mmol) was dissolved in methanol (5 ml) and treated with tri-n-butylamine (2 ml, 8.4 mmol). The solution was evaporated to dryness, dissolved in methanol and re-evaporated twice. Subsequently, this procedure was repeated three times with anhydrous DMF (20 ml) using an oil pump. The residue was dissolved in 12 ml anhydrous DMF, iodomethane (50 ml, 803 mmol) was added and the reaction mixture was stirred at room temperature for 2 h. The solution was evaporated to dryness, the residue dissolved in water (250 ml) and the pH of the solution adjusted from 1.2 to 7.5 with 1M triethylammonium bicarbonate pH 11.0. Purification by ion exchange chromatography yielded the product (105 mg) and the non-methylated compound (240 mg) as triethylammonium salts. The product was subsequently purified by RP HPLC and precipitated as its sodium salt (32 mg, 0.035 mmol, 12.6%). MS (ES): m/z 838 [M-H]$^-$, 941 [M+C$_6$H$_{15}$N]$^+$, 1042 [M+2×C$_6$H$_{15}$N]$^+$.

EXAMPLE 7

Preparation of Compound D

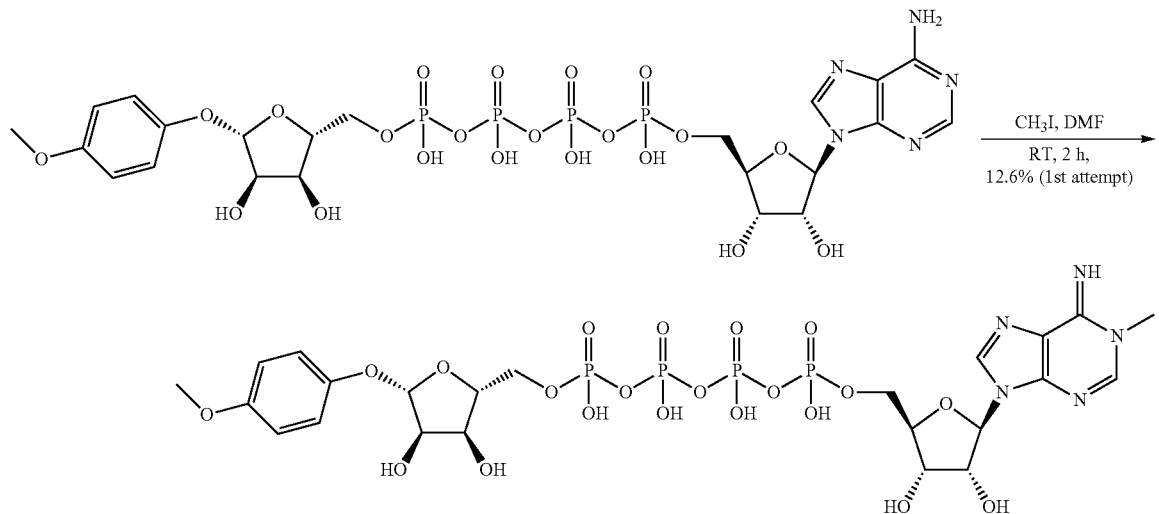

EXAMPLE 8

Preparation of Adenosine-5'-triphosphoroimidazolate

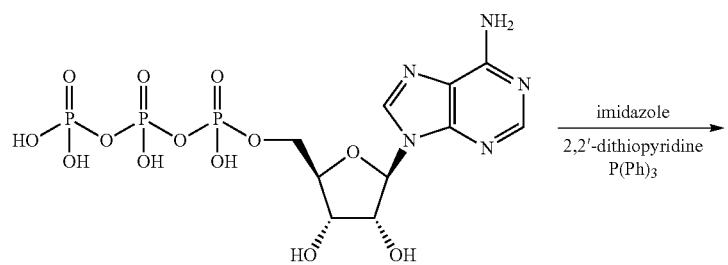

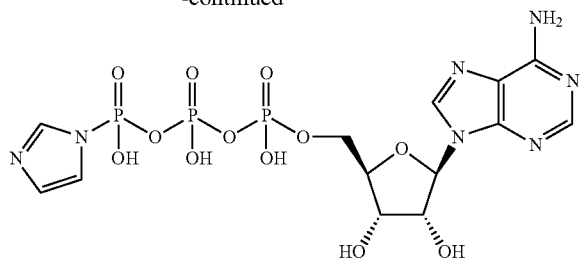

Adenosine-5'-triphosphate, sodium salt, (18.1 mmol) was dissolved in water (40 ml), the solution was applied to a column of Dowex 50WX8 (200 ml) in its pyridinium form, and eluted with a water methanol mixture (1:1, 500 ml). The elute was directly added drop wise to a cooled (ice water) and stirred solution of tri-n-butylamine (37.7 ml, 158.4 mmol) in 100 ml methanol. The solution was evaporated to dryness and re-evaporated twice with methanol and finally with anhydrous DMF (200 ml) using an oil pump. The residue was dissolved in 200 ml anhydrous DMF, imidazole (12.2 g, 180 mmol) 2,2'-dithiopyridine (31.6 g, 144 mmol) and triphenylphosphine (37.7 g, 144 mmol) were added and the solution was stirred 4 hours at room temperature. The solution was treated with 100 ml of a 1M sodium perchlorate solution in acetone and 30 ml acetone. The sodium salt of adenosine-5'-triphosphoroimidazolate was obtained as white precipitate, which was collected by centrifugation, washed with acetone (5×200 ml) and dried in a desiccator. The product (10.5 g, 17.4 mmol, 96%) was used in the next step without further purification.

EXAMPLE 9

Preparation of Compound C

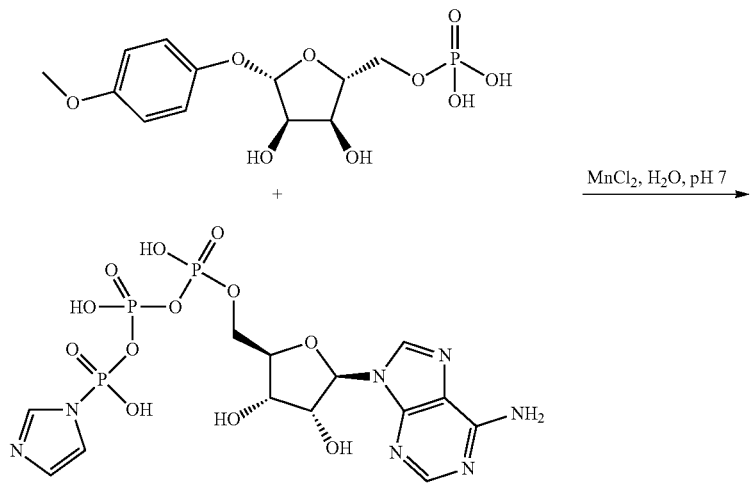

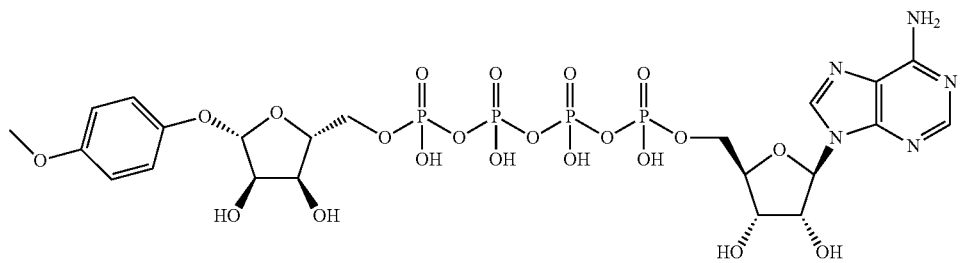

4-Methoxyphenyl-β-D-ribofuranosid-5'-monophosphate, sodium salt, (2.61 mmol) was dissolved in water (3 ml) and $MnCl_2 \times 2H_2O$ (1.26 g, 7.83 mmol) was added. The resulting solution was slowly added to a solution of adenosine-5'-triphosphorimidazolate (4.8 g, 7.8 mmol) in 0.2 M N-ethyl-morpholine-HCl buffer pH 7.0 (7 ml). The suspension (pH 4.5) was treated carefully with a 2 M HCl solution until the precipitation dissolved almost completely (pH 2.0). The reaction mixture was stirred over night at room temperature. The reaction mixture was then treated with a 1M versenol solution until the suspension became clear. Subsequently, it was diluted to 2000 ml, the pH adjusted to 7.5 and the solution applied to an ion exchange chromatography column. The fractions containing the product were pooled and the product was isolated as triethylammonium salt (136 mg, 0.11 mmol, 4%), which was used in the next step without further purification. MS (ES) m/z 824 [M-H]⁻.

EXAMPLE 10

Preparation of 4-Methoxyphenyl(tri-o-acetyl-α,β-D-ribofuranoside)

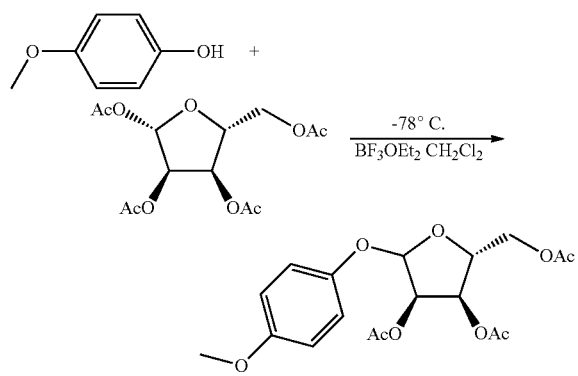

To a solution of 1,2,3,5-tetra-O-acetyl-β-D-ribofuranose (9 g, 28 mmol) in 120 mL of dichloromethane at −78° C. was added dropwise 3.52 ml of boron trifluoride diethyl etherate (28 mmol, 1 equiv.). The resulting mixture was stirred at −78° C. for 30 min. and 3.48 g of 4-methoxyphenol (28 mmol, 1 equiv.) was added. The mixture was slowly warmed to RT and stirred overnight. 300 ml of saturated sodium bicarbonate solution was added. The organic layer was separated. The water layer was extracted with dichloromethane twice (250 ml). The combined organic layer was washed with brine and dried over sodium sulfate. The solvents were removed under reduced pressure and the crude material was recrystallization from hexanes/ethyl acetate (30%) to afford 6.9 g of β-isomer product (64%)

EXAMPLE 11

Preparation of 4-Methoxyphenyl-β-D-ribofuranoside

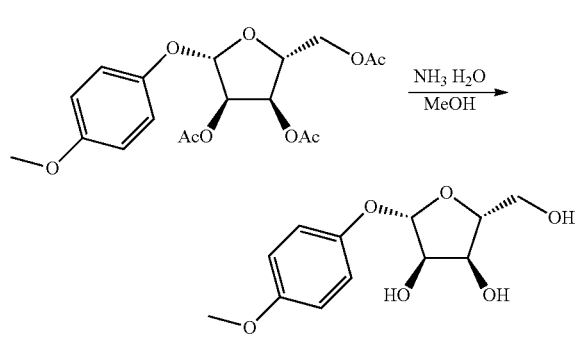

The mixture of 4-methoxyphenyl(tri-O-acetyl-β-D-ribofuranose (6.78 g, 17.75 mmol) and 40 ml of 28% ammonium hydroxide solution in 120 ml of methanol was stirred for 72 h. The solvents were removed under reduced pressure. The residue was co-evaporated with ethanol twice (50 ml). The residue was purified by flash column using 10% methanol/chloroform to afford 4.54 g of product (100%).

EXAMPLE 12

Preparation of Trimethylammonium salt of 4-Methoxyphenyl-β-D-ribofuranosid-5'-monophosphate

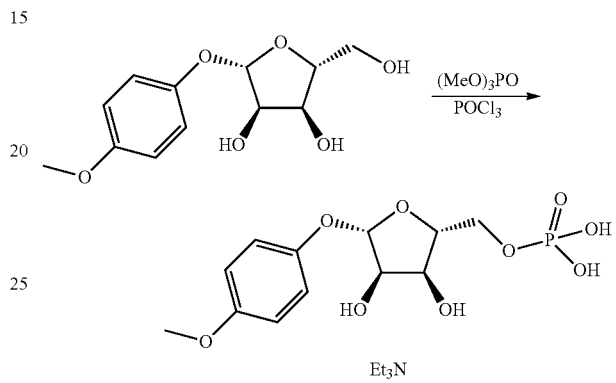

The triol (0.45 g, 1.758 mmol) was dissolved in 9 ml of trimethyl phosphate at 0° C. 0.22 ml of phosphorus (V) oxychloride (2.4 mmol, 1.35 equiv.) was added at 0° C. The mixture was stirred at 0° C. for five hours. 10 ml of water was added. The mixture was stirred overnight at RT. The mixture was then purified by HPLC to afforded 650 mg of the triethylammonium salt (84%). The same procedure has been used on 2-5 g scale with 80-90% yields.

EXAMPLE 13

Preparation of Morpholine Derivative of Intermediate E

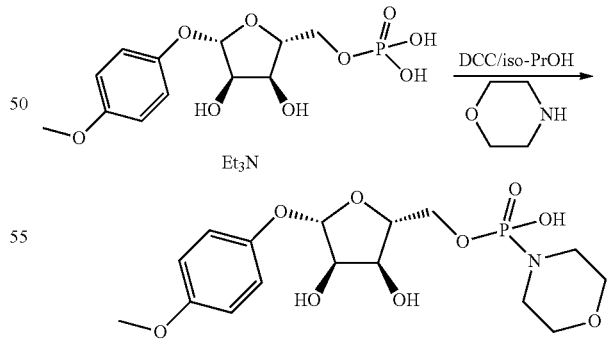

A solution of N,N'-dicyclohexylcarbodiimide (1.03 g, 5 mmol) in 15 ml of 2-propanol was added dropwise to the refluxed mixture of 4-methoxyphenyl-β-D-ribofuranosid-5'-monophosphate triethylammonium salt (437 mg, 1.07 mmol) and morpholine (435 mg, 5 mmol) in 20 ml of 2-propanol over 30 min. The resulting mixture was refluxed overnight. The solvent was removed under reduced pressure. 30 ml of water was added and the crude mixture was filtered to remove the white solid. The filtrate was extracted with ethyl acetate (3×20 ml). The combined organic layer was concentrated under reduced pressure. The residue was distilled three times as an azeotropic mixture with toluene (3×15 ml) and then dried under high vacuum to afford 500 mg of the crude product, which was used directly in the subsequent coupling.

EXAMPLE 14

Preparation of Compound C

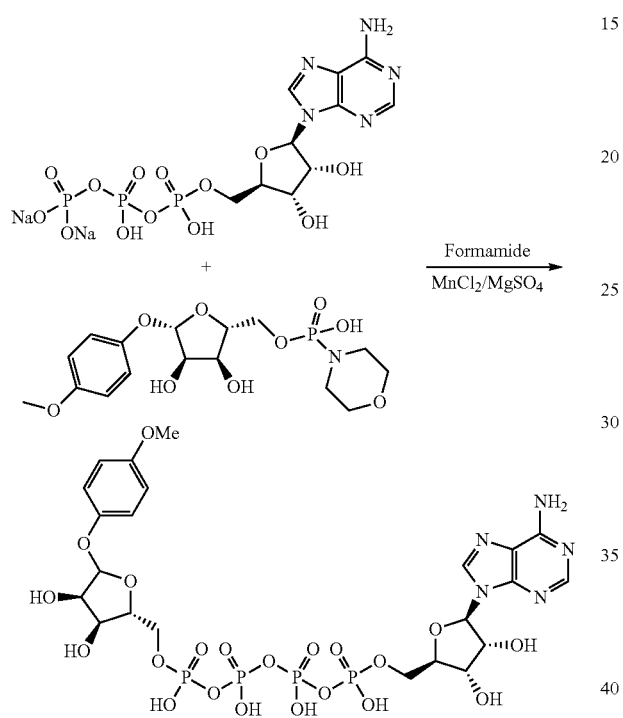

The mixture of 4-methoxyphenyl-β-D-ribofuranosid-5'-mono phosphormorpholine (crude 500 mg, ca. 107 mmol), disodium ATP (606.2 mg, 1.1 mmol), magnesium sulfate (168 mg, 1.4 mmol), 7 ml of a 0.2 M MnCl$_2$ (Manganese (II) chloride tetrahydrate) solution in formamide was stirred at room temperature over the weekend. The LC/Mass shows complete consumption of the mono-phosphate. 3 ml of a 1M versenol solution was added. The mixture was purified by HPLC to afford 430 mg of product in triethylammonium salt form.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of making an organophosphate compound, comprising admixing a compound of formula I-A and a compound of formula II-A to form a compound of formula III, wherein formula I-A is represented by:

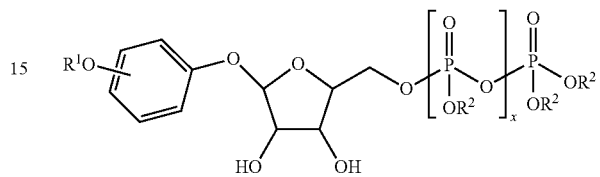

wherein:

R$^1$ is C$_1$-C$_4$ alkyl;

R$^2$ represents independently for each occurrence H or an alkali metal; or two occurrences of R$^2$ taken together form an alkaline earth metal; and x is 0, 1, or 2;

formula II-A is represented by:

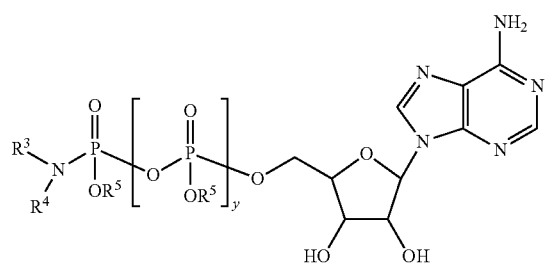

wherein:

R$^3$ and R$^4$, taken together with the nitrogen atom to which they are attached, form a 3 to 6 membered heterocyclic ring:

R$^5$ represents independently for each occurrence H or an alkali metal; or two occurrences of R$^5$ taken together form an alkaline earth metal;

y is 0, 1, or 2; and provided that the sum of x and y is 2; and formula III is represented by:

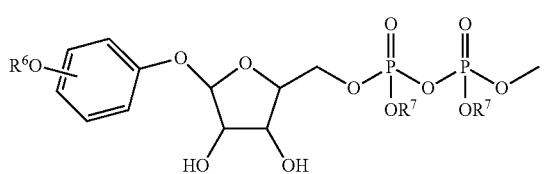

-continued (a)

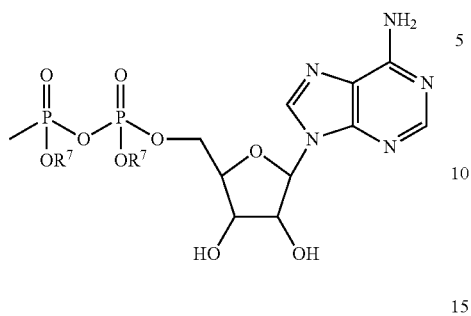

wherein:
R⁶ is $C_1$-$C_4$ alkyl; and
R⁷ represents independently for each occurrence H or an alkali metal; or two occurrences of R⁷ taken together form an alkaline earth metal.

2. The method of claim 1, wherein R⁷ is H, Na, or K.

3. The method of claim 1, wherein said compound of formula I-A is represented by one of the following:

(a)

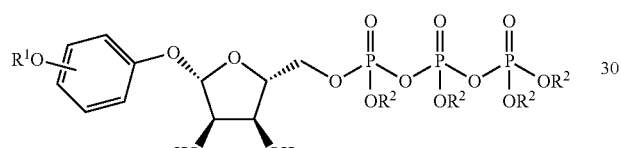

wherein:
R¹ is $C_1$-$C_4$ alkyl; and
R² represents independently for each occurrence H or an alkali metal;

(b)

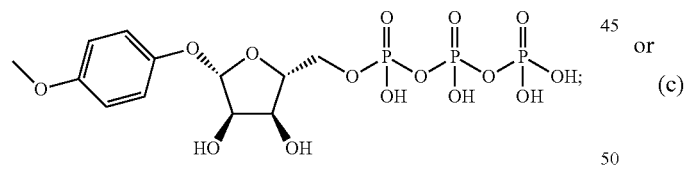

or (c)

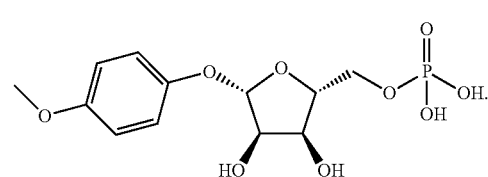 [SMILES: COc1ccc(O[C@@H]2O[C@H](COP(=O)(O)O)[C@@H](O)[C@H]2O)cc1]

4. The method of claim 1, wherein said compound of formula II-A is represented by one of the following:

(a)

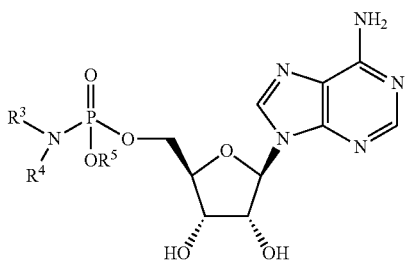

wherein:
R³ and R⁴, taken together with the nitrogen atom to which they are attached, form a 3 to 6 membered heterocyclic ring; and
R⁵ represents independently for each occurrence H or an alkali metal;

(b)

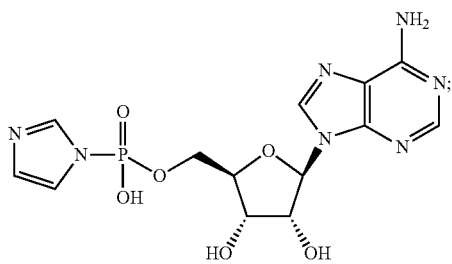 [SMILES: Nc1ncnc2c1ncn2[C@@H]1O[C@H](COP(=O)(O)n2ccnc2)[C@@H](O)[C@H]1O]

or (c)

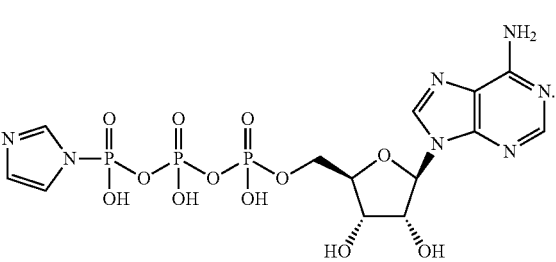 [SMILES: Nc1ncnc2c1ncn2[C@@H]1O[C@H](COP(=O)(O)OP(=O)(O)OP(=O)(O)n2ccnc2)[C@@H](O)[C@H]1O]

5. The method of claim 1, wherein said compound of formula III is represented by:

(a)

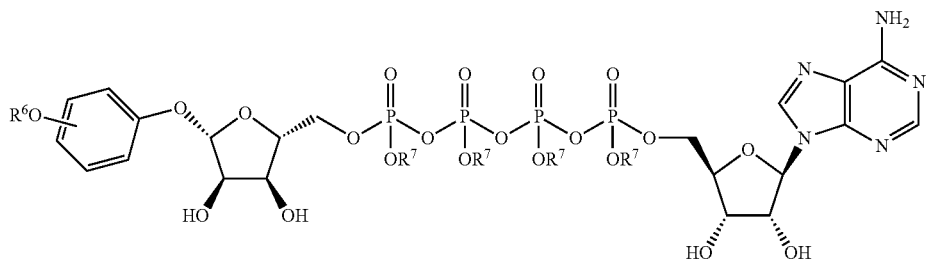

wherein:
R$^6$ is C$_1$-C$_4$ alkyl; and
R$^7$ represents independently for each occurrence H or an alkali metal; or (b)

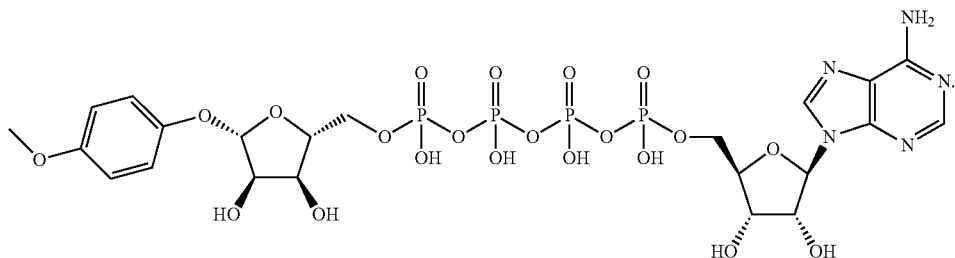 [SMILES: COc1ccc(O[C@@H]2O[C@H](COP(=O)(O)OP(=O)(O)OP(=O)(O)OP(=O)(O)OC[C@H]3O[C@@H](n4cnc5c(N)ncnc54)[C@H](O)[C@@H]3O)[C@@H](O)[C@H]2O)cc1]

6. The method of claim 1, further comprising admixing a Lewis acid.

7. The method of claim 6, wherein the Lewis acid is MnX$_2$, wherein X is halogen.

8. The method of claim 1, further comprising admixing a compound of formula III and an alkylating agent to form a compound of formula IV-A, wherein formula IV-A is represented by:

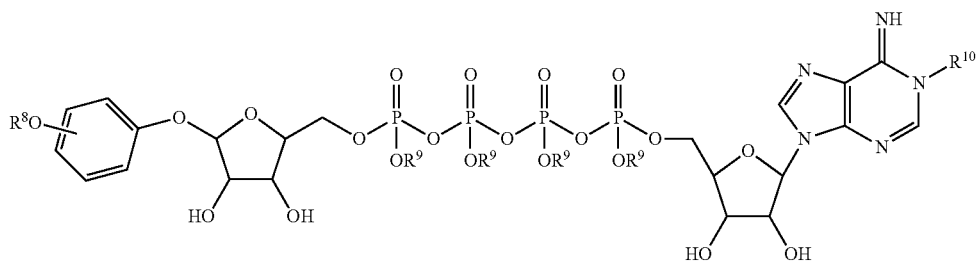

wherein:
R$^8$ and R$^{10}$ represent independently C$_1$-C$_4$ alkyl; and
R$^9$ represents independently for each occurrence H or an alkali metal; or two occurrences of R$^9$ taken together form an alkaline earth metal.

9. The method of claim 8, wherein said compound of formula IV-A is represented by:

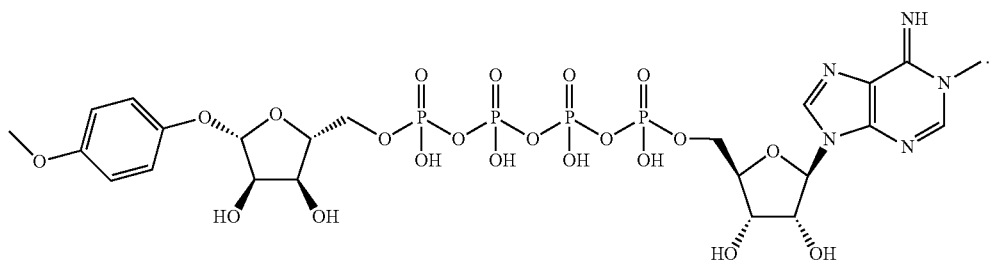

10. The method of claim 8, wherein the alkylating agent is Methyl-X, wherein X is selected from the group consisting of bromide, iodide, mesylate, tosylate, and triflate.

11. The method of claim 8, wherein said compound of formula I-A is represented by:

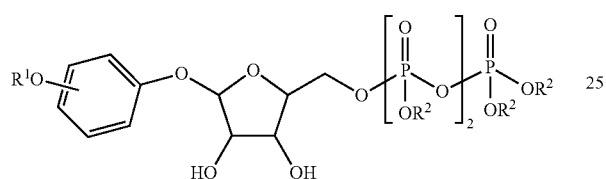

wherein:

$R^1$ is $C_1$-$C_4$ alkyl; and $R^2$ represents independently for each occurrence H or an alkali metal; or two occurrences of $R^2$ taken together form an alkaline earth metal.

12. The method of claim 8, optionally further comprising admixing a compound of formula V-A and R'O—P(O)(OR')—O—P(O)(OR')$_2$ and a phosphate coupling agent to form the compound of formula I-A, wherein R' is H or an alkali metal, and formula V-A is represented by:

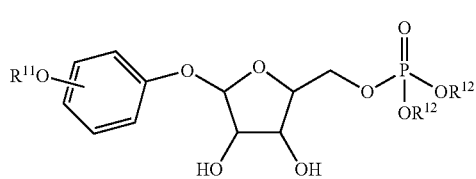

wherein:

$R^{11}$ is $C_1$-$C_4$ alkyl; and $R^{12}$ represents independently for each occurrence H or an alkali metal; or two occurrences of $R^{12}$ taken together form an alkaline earth metal.

13. The method of claim 12, wherein said compound of formula V-A is represented by one of the following:

(a)

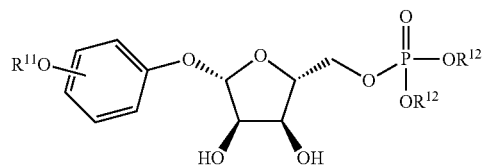

wherein:

$R^{11}$ is $C_1$-$C_4$ alkyl; and $R^{12}$ represents independently for each occurrence H or an alkali metal; or two occurrences of $R^{12}$ taken together form an alkaline earth metal; or (b)

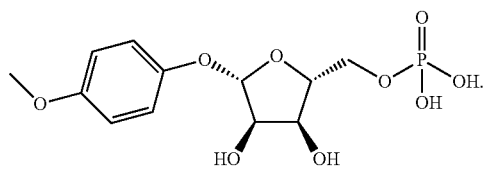 [SMILES: COc1ccc(O[C@@H]2O[C@H](COP(=O)(O)O)[C@@H](O)[C@H]2O)cc1]

14. The method of claim 8, wherein said phosphate coupling agent is 1,1'-carbonyldiimidazole.

15. The method of claim 12, further comprising admixing a compound of formula VI-A and a phosphorylating agent to form the compound of formula V-A, wherein formula VI-A is represented by:

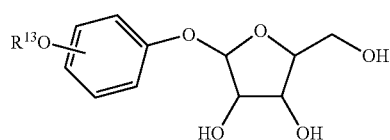

wherein $R^{13}$ is $C_1$-$C_4$ alkyl.

16. The method of claim 15, wherein said compound of formula VI-A is represented by:

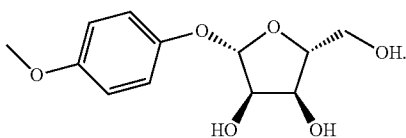 [SMILES: COc1ccc(O[C@@H]2O[C@H](CO)[C@@H](O)[C@H]2O)cc1]

17. The method of claim 15, wherein said phosphorylating agent is P(O)(O-alkyl)$_3$.

18. The method of claim 15, further comprising admixing a compound of formula VII-A and an acyl-deprotecting agent to form a compound of formula VI-A, wherein formula VII-A is represented by:

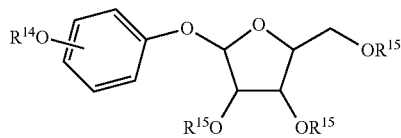

wherein:

$R^{14}$ is $C_1$-$C_4$ alkyl; and $R^{15}$ represents independently for each occurrence —C(O)alkyl, —C(O)aryl, or —C(O)aralkyl.

19. The method of claim 18, wherein said compound of formula VII-A is represented by:

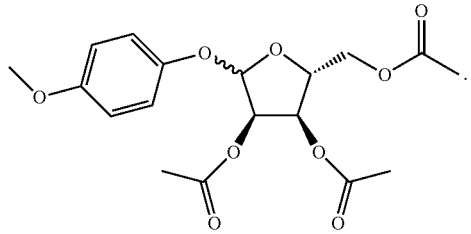 [SMILES: COc1ccc(OC2O[C@H](COC(C)=O)[C@@H](OC(C)=O)[C@H]2OC(C)=O)cc1]

20. The method of claim 18, wherein the acyl-deprotecting agent is a mixture of a base and a $C_1$-$C_6$ alcohol.

21. The method of claim 20, wherein the acyl-deprotecting agent is a mixture of $NH_3$ and MeOH.

22. The method of claim 18, further comprising admixing a compound of formula VIII-A, an alkoxyphenol, and a Lewis acid to form the compound of formula VII-A, wherein formula VIII-A is represented by:

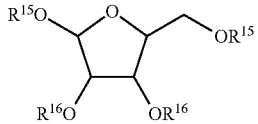

wherein $R^{16}$ represents independently for each occurrence —C(O)alkyl, —C(O)aryl, or —C(O)aralkyl.

23. The method of claim 21, wherein said Lewis acid is $SnCl_4$ or $TiCl_4$.

24. The method of claim 22, wherein said compound of formula VIII-A is represented by:

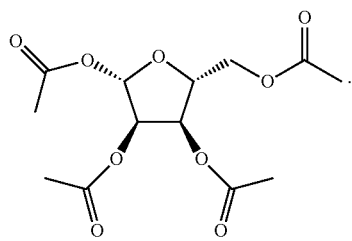 [SMILES: CC(=O)OC[C@H]1O[C@@H](OC(C)=O)[C@H](OC(C)=O)[C@@H]1OC(C)=O]

25. A method of making an organophosphate compound, comprising admixing a compound of formula I-C and a compound of formula II-C to form a compound of formula III, wherein formula I-C is represented by:

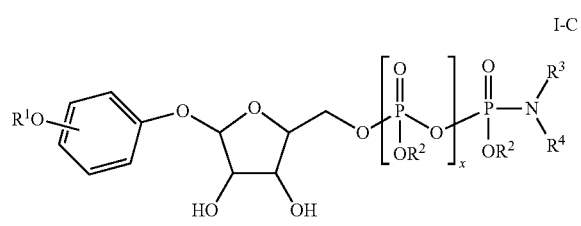

wherein:

$R^1$ is $C_1$-$C_4$ alkyl;

$R^2$ represents independently for each occurrence H or an alkali metal; or two occurrences of $R^2$ taken together form an alkaline earth metal;

$R^3$ and $R^4$, taken together with the nitrogen atom to which they are attached, form a 3 to 6 membered heterocyclic ring; and x is 0 or 1;

formula II-C is represented by:

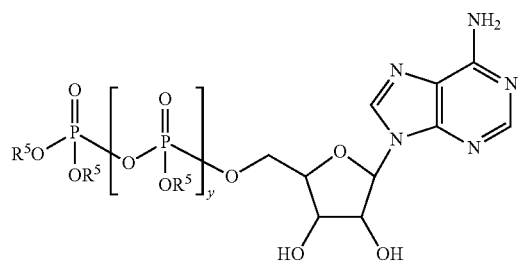

wherein:

$R^5$ represents independently for each occurrence H or an alkali metal; or two occurrences of $R^5$ taken together form an alkaline earth metal;

y is 1 or 2; and provided that the sum of x and y is 2; and formula III is represented by:

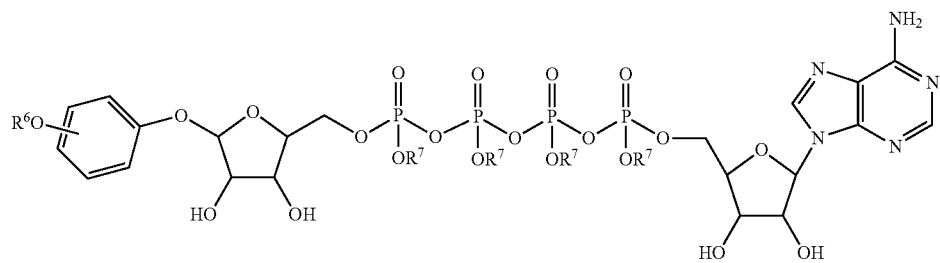

wherein:
$R^6$ is $C_1$-$C_4$ alkyl; and
$R^7$ represents independently for each occurrence H or an alkali metal; or two occurrences of $R^7$ taken together form an alkaline earth metal.

26. The method of claim 25, wherein $R^7$ is H, Na, or K.

27. The method of claim 25, wherein said compound of formula I-C is represented by one of the following:
(a)

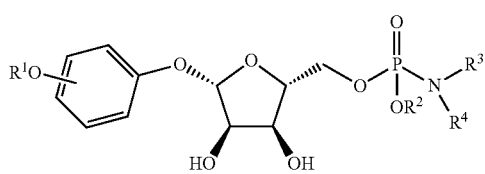

wherein:
$R^1$ is $C_1$-$C_4$ alkyl;
$R^2$ represents independently for each occurrence H or an alkali metal; and
$R^3$ and $R^4$, taken together with the nitrogen atom to which they are attached, form a 3 to 6 membered heterocyclic ring; or (b)

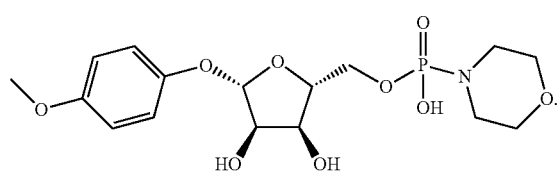 [SMILES: COc1ccc(O[C@@H]2O[C@H](COP(=O)(O)N3CCOCC3)[C@@H](O)[C@H]2O)cc1]

28. The method of claim 25, wherein said compound of formula II-C is represented by one of the following:

(a)

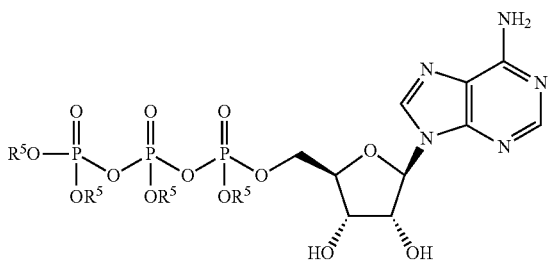

wherein $R^5$ represents independently for each occurrence H or an alkali metal; or (b)

wherein $R^5$ represents independently for each occurrence H or Na.

29. The method of claim 25, wherein said compound of formula III is represented by one of the following:

(a)

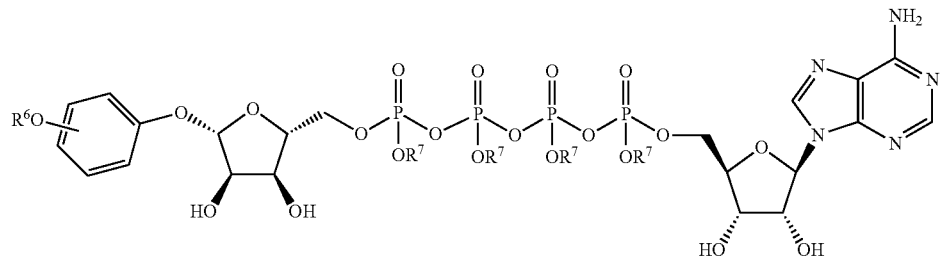

wherein:
R⁶ is $C_1$-$C_4$ alkyl; and
R⁷ represents independently for each occurrence H or an alkali metal; or (b)

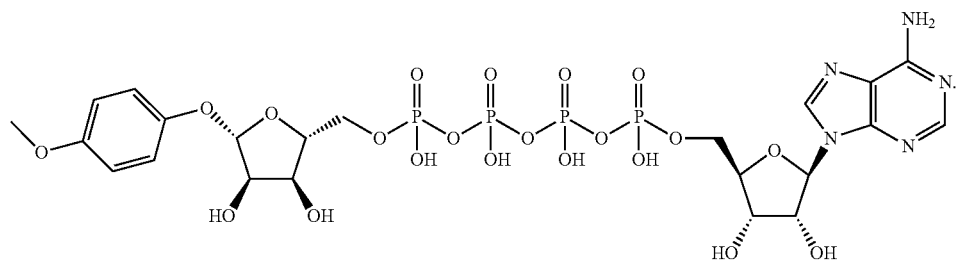 [SMILES: COc1ccc(O[C@@H]2O[C@H](COP(=O)(O)OP(=O)(O)OP(=O)(O)OP(=O)(O)OC[C@H]3O[C@@H](n4cnc5c(N)ncnc54)[C@H](O)[C@@H]3O)[C@@H](O)[C@H]2O)cc1]

30. The method of claim 25, further comprising admixing a Lewis acid.

31. The method of claim 30, wherein said Lewis acid is $MnCl_2$.

32. The method of claim 25, further comprising admixing a compound of formula III and an alkylating agent to form a compound of formula IV-C, wherein formula IV-C is represented by:

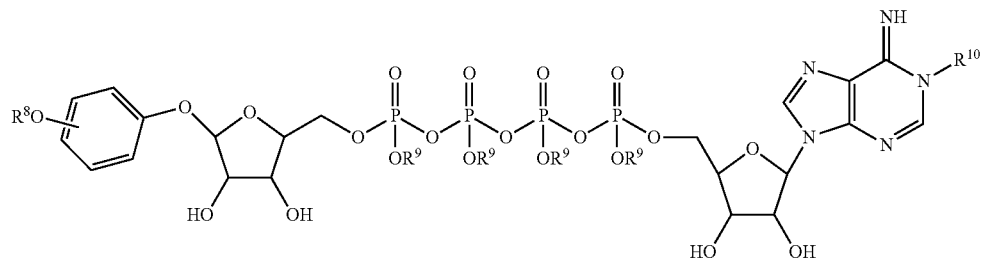

wherein:
R⁸ and R¹⁰ represent independently $C_1$-$C_4$ alkyl; and
R⁹ represents independently for each occurrence H or an alkali metal; or two occurrences of R⁹ taken together form an alkaline earth metal.

33. The method of claim 32, wherein said compound of formula IV-C is represented by:

34. The method of claim 32, wherein the alkylating agent is Methyl-X, wherein X is selected from the group consisting of bromide, iodide, mesylate, tosylate, and triflate.

35. The method of claim 32, further comprising admixing a compound of formula V-C and morpholine and a carbodiimide coupling agent to form the compound of formula I-C, wherein formula V-C is represented by:

And further comprising $N(R^{13})_4$ salts thereof;

wherein:

$R^{11}$ is C1-C4 alkyl;

$R^{12}$ represents independently for each occurrence H or an alkali metal; or two occurrences of $R^{12}$ taken together form an alkaline earth metal; and $R^{13}$ represents independently for each occurrence H or $C_1$-$C_4$ alkyl.

36. The method of claim 35, wherein said compound of formula V-C is represented by and further comprising $N(R^{13})_4$ salts thereof;

wherein:

$R^{11}$ is $C_1$-$C_4$ alkyl; and $R^{12}$ represents independently for each occurrence H or an alkali metal; or two occurrences of $R^{12}$ taken together form an alkaline earth metal; and $R^{13}$ represents independently for each occurrence H or $C_1$-$C_4$ alkyl.

37. The method of claim 35, wherein said compound of formula V-C is represented by:

38. The method of claim 35, wherein said carbodiimide coupling agent is N,N'-dicyclohexylcarbodiimide.

39. The method of claim 35, further comprising admixing a compound of formula VI-C and a phosphorylating agent to form the compound of formula V-C, wherein formula VI-C is represented by:

wherein, $R^{14}$ is $C_1$-$C_4$ alkyl.

40. The method of claim 39, wherein said compound of formula VI-C is represented by:

41. The method of claim 39, wherein said phosphorylating agent is $P(O)(O\text{-alkyl})_3$.

42. The method of claim 39, further comprising admixing a compound of formula VII-C and an acyl-deprotecting agent to form a compound of formula VI-C, wherein formula VII-C is represented by:

wherein:

$R^{15}$ is $C_1$-$C_4$ alkyl; and $R^{16}$ represents independently for each occurrence —C(O)alkyl, —C(O)aryl, or —C(O)aralkyl.

43. The method of claim 42, wherein said compound of formula VII-C is represented by:

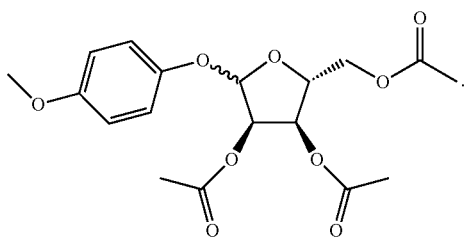 [SMILES: COc1ccc(OC2O[C@H](COC(C)=O)[C@@H](OC(C)=O)[C@H]2OC(C)=O)cc1]

44. The method of claim 42, wherein the acyl-deprotecting agent is a mixture of a base and a $C_1$-$C_6$ alcohol.

45. The method of claim 44, wherein the acyl-deprotecting agent is a mixture of $NH_3$ and MeOH.

46. The method of claim 42, further comprising admixing a compound of formula VIII-C, an alkoxyphenol, and a Lewis acid to form the compound of formula VII-C, wherein formula VIII-C is represented by:

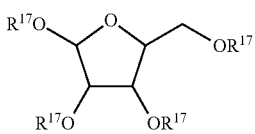

wherein $R^{17}$ represents independently for each occurrence —C(O)alkyl, —C(O)aryl, or —C(O)aralkyl.

47. The method of claim 46, wherein said compound of formula VIII-C is represented by:

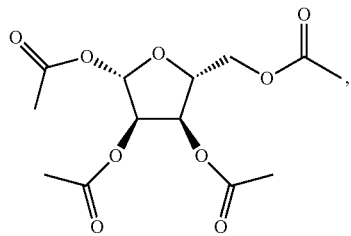 [SMILES: CC(=O)OC[C@H]1O[C@@H](OC(C)=O)[C@H](OC(C)=O)[C@@H]1OC(C)=O]

48. The method of claim 46, wherein said Lewis acid is $BF_3.OEt_2$.

49. A method of making an organophosphate compound, comprising admixing a compound of formula I-D and a compound of formula II-D to form a compound of formula III-D, wherein formula I-D is represented by:

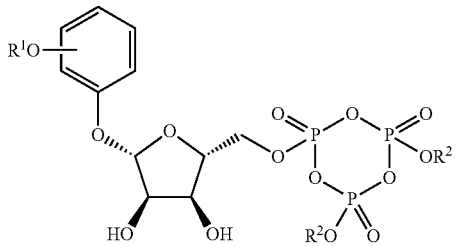

wherein:

$R^1$ is $C_1$-$C_4$ alkyl;

$R^2$ represents independently for each occurrence H, an alkali metal, or $N(R^3)_4$; and $R^3$ represents independently for each occurrence H or $C_1$-$C_6$ alkyl; formula II-D is represented by:

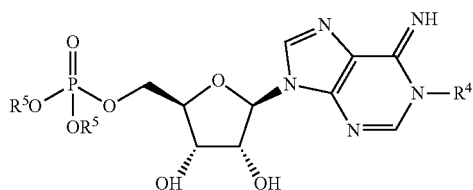

wherein:

$R^4$ is $C_1$-$C_4$ alkyl;

$R^5$ represents independently for each occurrence H, an alkali metal, or $N(R^6)_4$; and $R^6$ represents independently for each occurrence H or $C_1$-$C_6$ alkyl; and formula III-D is represented by:

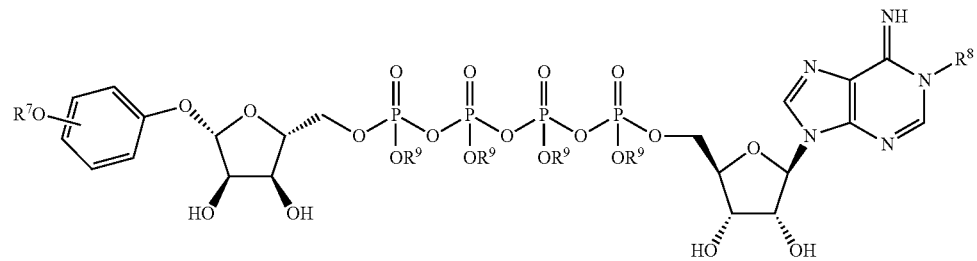

wherein:
R$^7$ and R$^8$ are independently C$_1$-C$_4$ alkyl;
R$^9$ represents independently for each occurrence H, an alkali metal, or N(R$^{10}$)$_4$; and
R$^{10}$ represents independently for each occurrence H or C$_1$-C$_6$ alkyl.

50. The method of claim 49, further comprising admixing a Lewis acid.

51. The method of claim 50, wherein said Lewis acid is ZnX$_2$, and X is halogen.

52. The method of claim 49, further comprising admixing a compound of formula IV-D and an alkylating agent to form said compound of formula II-D, wherein formula IV-D is represented by:

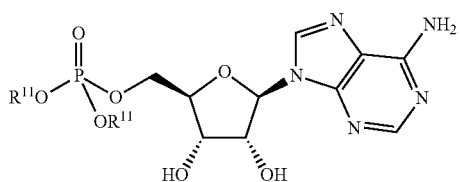

wherein R$^{11}$ represents independently for each occurrence H or an alkali metal.

53. The method of claim 52, wherein said alkylating agent is SO$_2$(OR')$_2$ wherein R' is C$_1$-C$_4$ alkyl.

54. The method of claim 49, further comprising admixing a compound of formula V-D and a phosphorylating agent to form said compound of formula I-D, wherein formula V-D is represented by:

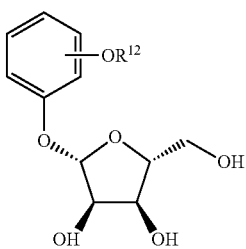

wherein, R$^{12}$ is C$_1$-C$_4$ alkyl.

55. The method of claim 54, wherein said method comprises admixing said compound of formula V-D and P(O)(OR')$_3$ and then admixing (OR")$_2$P(O)OP(O)(OR")$_2$, wherein R' is C$_1$-C$_4$ alkyl, R" is H or N(R'")$_4$, and R'" represents independently for each occurrence H or C$_1$-C$_4$ alkyl.

56. The method of claim 54, further comprising hydrolyzing a compound of formula VI-D to form compound of formula V-D, wherein formula VI-D is represented by:

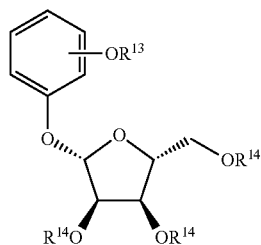

wherein:
R$^{13}$ is C$_1$-C$_4$ alkyl; and
R$^{14}$ represents independently for each occurrence —C(O)alkyl, —C(O)aryl, or —C(O)aralkyl.

57. The method of claim 56, further comprising admixing a compound of formula VII-D, a compound of formula VIII-D, and a Lewis acid to form said compound of formula VI-D, wherein formula VII-D is presented by:

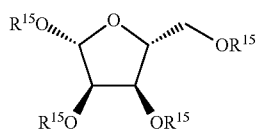

wherein R$^{15}$ represents independently for each occurrence —C(O)alkyl, —C(O)aryl, or —C(O)aralkyl; and
formula VIII-D is represented by:

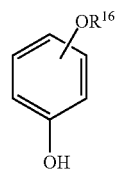

wherein R$^{16}$ is C$_1$-C$_4$ alkyl.

58. A method of making an organophosphate compound, comprising admixing, a compound of formula I-E and a compound of formula II-E to form a compound of formula III-E, wherein formula I-E is represented by:

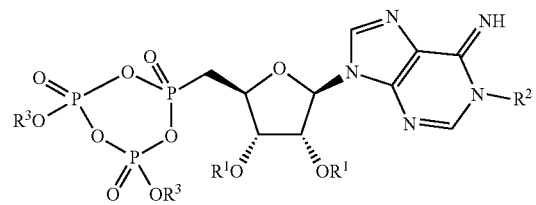

wherein:
R$^1$ represents independently for each occurrence H, —C(O)alkyl, —C(O)aryl, or —C(O)aralkyl;
R$^2$ is C$_1$-C$_4$ alkyl;
R$^3$ represents independently for each occurrence H, an alkali metal, or N(R$^4$)$_4$; and
R$^4$ represents independently for each occurrence H or C$_1$-C$_6$ alkyl; formula II-E is represented by:

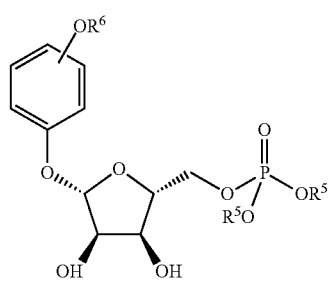

wherein:
  $R^5$ represents independently for each occurrence H, an alkali metal, or $N(R^7)_4$;
  $R^6$ is $C_1$-$C_4$ alkyl; and
  $R^7$ represents independently for each occurrence H or $C_1$-$C_6$ alkyl; and formula III-E is represented by:

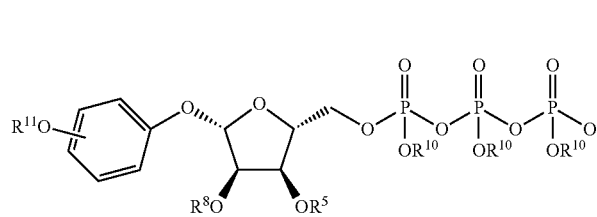

wherein:
  $R^8$ represents independently for each occurrence H, —C(O)alkyl, —C(O)aryl, or —C(O)aralkyl;
  $R^9$ and $R^{11}$ represent independently $C_1$-$C_4$ alkyl;
  $R^{10}$ represents independently for each occurrence H, an alkali metal, or $N(R^{12})_4$; and
  $R^{12}$ represents independently for each occurrence H or $C_1$-$C_6$ alkyl.

59. The method of claim 58, further comprising admixing a Lewis acid.

60. The method of claim 59, wherein the Lewis acid is $ZnCl_2$.

61. The method of claim 58, further comprising admixing an acyl-deprotecting agent and said compound of formula III-E.

62. The method of claim 61, wherein said acyl-deprotecting agent is a base and $C_1$-$C_6$ alcohol.

63. The method of claim 58, further comprising admixing a compound of formula IV-E and an oxidizing agent to form I-E, wherein formula IV-E is represented by

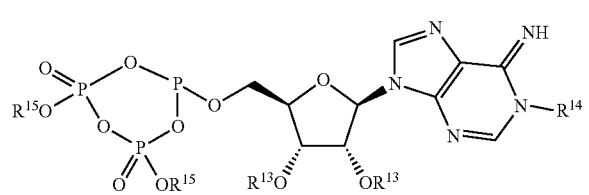

wherein:
  $R^{13}$ is H, —C(O)alkyl, —C(O)aryl, or —C(O)aralkyl;
  $R^{14}$ is $C_1$-$C_4$ alkyl;
  $R^{15}$ represents independently for each occurrence H, an alkali metal, or $N(R^{16})_4$; and
  $R^{16}$ represents independently for each occurrence H or $C_1$-$C_6$ alkyl.

64. The method of claim 63, wherein said oxidizing agent is iodine.

65. The method of claim 63, further comprising admixing a compound of formula V-E and phosphorylating agent to form a compound of formula IV-E, wherein formula V-E is represented by:

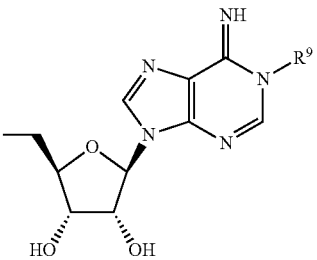

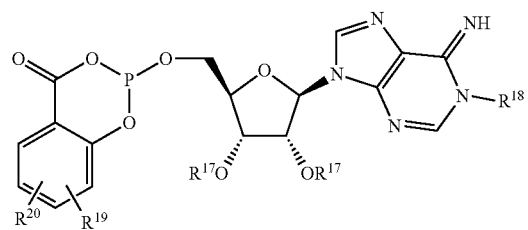

wherein:
  $R^{17}$ is H, —C(O)alkyl, —C(O)aryl, or —C(O)aralkyl;
  $R^{18}$ is $C_1$-$C_4$ alkyl; and
  $R^{19}$ and $R^{20}$ are independently alkyl, alkoxy, halogen, aryl, or aralkyl, or $R^{19}$ and $R^{20}$ taken with the aryl group to which they are attached, form a fused aromatic group.

66. The method of claim 65, wherein said phosphorylating agent is pyrophosphate.

67. The method of claim 65, further comprising admixing a compound of formula VI-E and a compound of formula VII-E to form a compound of formula V-E, wherein formula VI-E is represented by:

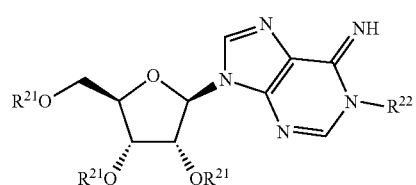

wherein:
  $R^2$ is H, —C(O)alkyl, —C(O)aryl, or —C(O)aralkyl; and
  $R^{22}$ is $C_1$-$C_4$ alkyl; and formula VII-E is represented by:

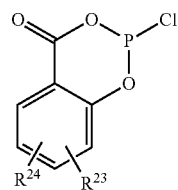

wherein:
$R^{23}$ and $R^{24}$ are independently alkyl, alkoxy, halogen, aryl, or aralkyl, or $R^{23}$ and $R^{24}$ taken with the aryl group to which they are attached, form a fused aromatic group.

68. The method of 67, further comprising admixing a compound of formula VIII-E and an alkylating agent to form a compound of formula VI-E, wherein formula VIII-E is represented by:

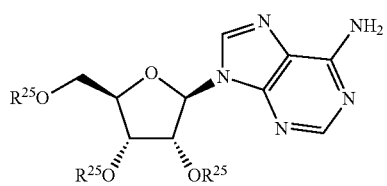

wherein, $R^{25}$ is H, —C(O)CH$_3$, or —C(O)CH$_2$-phenyl.

69. The method of claim 68, wherein said alkylating agent is methyl iodide.

70. A compound represented by the following formula:

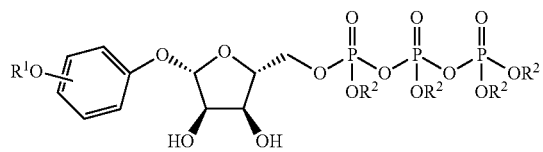

wherein:
$R^1$ is $C_1$-$C_4$ alkyl; and
$R^2$ represents independently for each occurrence H or an alkali metal.

71. A compound represented by the following formula:

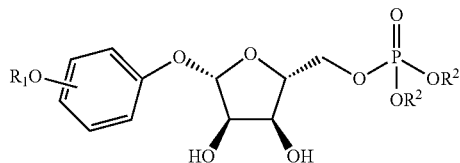

wherein:
$R_1$ is $C_1$-$C_4$ alkyl; and
$R^2$ represents independently for each occurrence H or an alkali metal; or two occurrences of $R^2$ taken together form an alkaline earth metal.

72. A compound represented by the following formula:

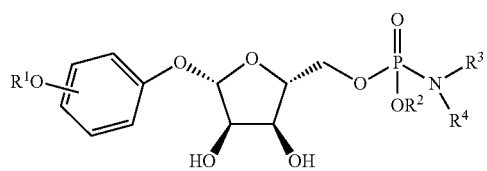

wherein:
$R^1$ is $C_1$-$C_4$ alkyl;
$R^2$ represents independently for each occurrence H or an alkali metal; and
$R^3$ and $R^4$, taken together with the nitrogen atom to which they are attached, form a 3 to 6 membered heterocyclic ring.

* * * * *